US008134023B2

(12) United States Patent
Hu et al.

(10) Patent No.: US 8,134,023 B2
(45) Date of Patent: Mar. 13, 2012

(54) PREPARATION OF PREGABALIN AND RELATED COMPOUNDS

(75) Inventors: Shanghui Hu, San Diego, CA (US); Carlos Alberto Martinez, Oceanside, CA (US); Junhua Tao, San Diego, CA (US); William Eugene Tully, Loughbeg (IE); Patrick Kelleher, Ringaskiddy (IE); Yves Dumond, Ringaskiddy (IE)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 13/247,032

(22) Filed: Sep. 28, 2011

(65) Prior Publication Data

US 2012/0015412 A1 Jan. 19, 2012

Related U.S. Application Data

(63) Continuation of application No. 12/951,429, filed on Nov. 22, 2010, now Pat. No. 8,044,227, which is a continuation of application No. 12/254,336, filed on Oct. 20, 2008, now Pat. No. 7,838,686, which is a continuation of application No. 11/157,585, filed on Jun. 21, 2005, now abandoned.

(60) Provisional application No. 60/629,034, filed on Nov. 18, 2004, provisional application No. 60/581,671, filed on Jun. 21, 2004.

(51) Int. Cl.
*C07C 255/15* (2006.01)
*C07C 229/08* (2006.01)

(52) U.S. Cl. ........................ 558/441; 562/553

(58) Field of Classification Search .................. 558/441; 562/553
See application file for complete search history.

(56) References Cited

U.S. PATENT DOCUMENTS

| | | | |
|---|---|---|---|
| 5,563,175 A | 10/1996 | Silverman et al. | 514/561 |
| 5,599,973 A | 2/1997 | Silverman et al. | 562/443 |
| 5,608,090 A | 3/1997 | Silverman et al. | 552/10 |
| 5,616,793 A | 4/1997 | Huckabee et al. | 562/553 |
| 5,618,710 A | 4/1997 | Navia et al. | 435/174 |
| 5,629,447 A | 5/1997 | Huckabee et al. | 562/553 |
| 5,637,767 A * | 6/1997 | Grote et al. | 562/553 |
| 5,684,189 A | 11/1997 | Silverman et al. | 562/553 |
| 5,710,304 A | 1/1998 | Silverman et al. | 558/52 |
| 5,840,956 A | 11/1998 | Grote et al. | 558/441 |
| 5,847,151 A | 12/1998 | Silverman et al. | 548/230 |
| 6,001,876 A | 12/1999 | Singh | 514/561 |
| 6,028,214 A | 2/2000 | Silverman et al. | 560/188 |
| 6,046,353 A | 4/2000 | Grote et al. | 558/442 |
| 6,127,418 A | 10/2000 | Bueno et al. | 514/561 |
| 6,194,459 B1 | 2/2001 | Akunne et al. | 514/561 |
| 6,242,488 B1 | 6/2001 | Bueno et al. | 514/561 |
| 6,306,910 B1 | 10/2001 | Magnus et al. | 514/561 |
| 6,326,374 B1 | 12/2001 | Magnus et al. | 514/264 |
| 6,329,429 B1 | 12/2001 | Schrier et al. | 514/561 |
| 6,359,005 B1 | 3/2002 | Pande | 514/561 |
| 6,359,169 B1 | 3/2002 | Silverman et al. | 560/190 |
| 6,426,368 B2 | 7/2002 | Bueno et al. | 514/561 |
| 2003/0149172 A1 | 8/2003 | Cao et al. | 525/54.1 |
| 2003/0212290 A1 | 11/2003 | Burk et al. | 558/441 |

OTHER PUBLICATIONS

Anderson et al., One Biocatalyst—Many Applications: The Use of Candida Antarctica B-Lipase in Organic Synthesis, *Biocat. Biotransform*, (1998), vol. 16, pp. 181-204.
Berge, et al, Pharmaceutical Salts, *J. of Pharm. Sci.*, (1977), vol. 66, pp. 1-19.
Burk et al, An Enantioselective Synthesis of (S)-(+)-3-Aminomethyl-5-methylhexanoic Acid via Asymmetric Hydrogenation, *J. Org. Chem.*, (2003), pp. 5731-5734, vol. 68.
Haleblian, Characterization of Habits and Crystalline Modification of Solids and Their Pharmaceutical Applications, *J. of Pharm. Sci.*, (1975), vol. 64, pp. 1269-1288.
Kato et al, *Nippon Noqei Kaqaku Kaishi*, (1953), p. 500, vol. 27 (in Japanese, translated to English).
Knabe, J. et al, *Arch. Pharm*, (1972), pp. 757-765, vol. 305 (in German, translated to English).
Knabe, J. et al, *Tetrahedron Lett.*, (1973), pp. 745-746, vol. 10 (in German, translated to English).
Knabe, J., et al, *Arch. Pharm.*, (1984), pp. 353-362, vol. 317, No. 4.
Koeller et al., Enzymes for Chemical Synthesis, *Nature*, (2001), vol. 409, pp. 232-240.
Lopez-Serrano et al., Cross-linked Enzyme Aggregates with Enhanced Activity: Application to Lipases, *Biotech. Lett.*, (2002), vol. 24, pp. 1379-1383.
Sammis et al, Highly Enantioselective, Catalytic Conjugate Addition of Cyanide to alpha, beta-Unsaturated Imides, *J. Am. Chem. Soc.*, (2003), pp. 4442-4443, vol. 125.
Wilk, The Knoevenagel Condensation of O,S- and S,S-Diethyl Malonates and Ethyl Pyruvate, *Tetrahedron*, (1997), vol. 53, pp. 7097-7100.
Yazbeck et al., Automated Enzyme Screening Methods for the Perparation of Enantiopure Pharmacutical Intermediates, *Synth. Catal.*, (2003), vol. 345, pp. 524-532.

* cited by examiner

*Primary Examiner* — Joseph Kosack
(74) *Attorney, Agent, or Firm* — J. Michael Dixon; Gregg C. Benson

(57) ABSTRACT

Materials and methods for preparing (S)-(+)-3-aminomethyl-5-methyl-hexanoic acid and structurally related compounds via enzymatic kinetic resolution are disclosed.

1 Claim, 2 Drawing Sheets

PREPARATION OF PREGABALIN AND RELATED COMPOUNDS

CROSS REFERENCE TO RELATED APPLICATIONS

Cross Reference

This application is a continuation of U.S. application Ser. No. 12/951,429, filed Nov. 22, 2010; which was a continuation of U.S. application Ser. No. 12/254,336, filed Oct. 20, 2008, now U.S. Pat. No. 7,838,686, which claims the benefits of U.S. application Ser. No. 11/157,585, filed Jun. 21, 2005, which claims priority under 35 U.S.C. §119(e) to U.S. Provisional Patent Application Nos. 60/629,034, filed Nov. 18, 2004 and 60/581,671, filed Jun. 21, 2004, the contents of each which are incorporated by reference.

BACKGROUND OF THE INVENTION

1. Field of Invention

This invention relates to methods and materials for preparing enantiomerically-enriched γ-amino acids via enzymatic kinetic resolution, and is particularly useful for preparing γ-amino acids that exhibit binding affinity to the human $\alpha_2\delta$ calcium channel subunit, including pregabalin and related compounds.

2. Discussion

Pregabalin, (S)-(+)-3-aminomethyl-5-methyl-hexanoic acid, is related to the endogenous inhibitory neurotransmitter γ-aminobutyric acid (GABA), which is involved in the regulation of brain neuronal activity. Pregabalin exhibits anti-seizure activity, as discussed in U.S. Pat. No. 5,563,175 to R. B. Silverman et al., and is thought to be useful for treating, among other conditions, pain, physiological conditions associated with psychomotor stimulants, inflammation, gastrointestinal damage, alcoholism, insomnia, and various psychiatric disorders, including mania and bipolar disorder. See, respectively, U.S. Pat. No. 6,242,488 to L. Bueno et al., U.S. Pat. No. 6,326,374 to L. Magnus & C. A. Segal, and U.S. Pat. No. 6,001,876 to L. Singh; U.S. Pat. No. 6,194,459 to H. C. Akunne et al.; U.S. Pat. No. 6,329,429 to D. Schrier et al.; U.S. Pat. No. 6,127,418 to L. Bueno et al.; U.S. Pat. No. 6,426,368 to L. Bueno et al.; U.S. Pat. No. 6,306,910 to L. Magnus & C. A. Segal; and U.S. Pat. No. 6,359,005 to A. C. Pande, which are herein incorporated by reference in their entirety and for all purposes.

Pregabalin has been prepared in various ways. Typically, a racemic mixture of 3-aminomethyl-5-methyl-hexanoic acid is synthesized and subsequently resolved into its R- and S-enantiomers. Such methods may employ an azide intermediate, a malonate intermediate, or Hofman synthesis. See, respectively, U.S. Pat. No. 5,563,175 to R. B. Silverman et al.; U.S. Pat. Nos. 6,046,353, 5,840,956, and 5,637,767 to T. M. Grote et al.; and U.S. Pat. Nos. 5,629,447 and 5,616,793 to B. K. Huckabee & D. M. Sobieray, which are herein incorporated by reference in their entirety and for all purposes. In each of these methods, the racemate is reacted with a chiral acid (a resolving agent) to form a pair of diastereoisomeric salts, which are separated by known techniques, such as fractional crystallization and chromatography. These methods thus involve significant processing beyond the preparation of the racemate, which along with the resolving agent, adds to production costs. Moreover, the undesired R-enantiomer is frequently discarded since it cannot be efficiently recycled, thereby reducing the effective throughput of the process by 50%.

Pregabalin has also been synthesized directly using a chiral auxiliary, (4R,5S)-4-methyl-5-phenyl-2-oxazolidinone. See, e.g., U.S. Pat. Nos. 6,359,169, 6,028,214, 5,847,151, 5,710,304, 5,684,189, 5,608,090, and 5,599,973, all to R. B. Silverman et al, which are herein incorporated by reference in their entirety and for all purposes. Although these methods provide pregabalin in high enantiomeric purity, they are less desirable for large-scale synthesis because they employ comparatively costly reagents (e.g., the chiral auxiliary) that are difficult to handle, as well as special cryogenic equipment to reach required operating temperatures, which can be as low as −78° C.

A recently published U.S. patent application discusses a method of making pregabalin via asymmetric hydrogenation of a cyano-substituted olefin to produce a chiral cyano precursor of (S)-3-aminomethyl-5-methylhexanoic acid. See commonly assigned U.S. Patent Application No. 2003/0212290 A1 to Burk et al., published Nov. 13, 2003, which is herein incorporated by reference in its entirety for all purposes. The cyano precursor is subsequently reduced to give pregabalin. The asymmetric hydrogenation employs a chiral catalyst that is comprised of a transition metal bound to a bisphosphine ligand, such as (R,R)-Me-DUPHOS. The method results in substantial enrichment of pregabalin over (R)-3-(aminomethyl)-5-methylhexanoic acid.

The method discussed in U.S. Patent Application No. 2003/0212290 A1 represents a commercially viable method for preparing pregabalin, but further improvements would be desirable for various reasons. For example, bisphosphine ligands, including the proprietary ligand (R,R)-Me-DU-PHOS, are often difficult to prepare because they possess two chiral centers, which adds to their cost. Furthermore, asymmetric hydrogenation requires the use of special equipment capable of handling $H_2$, which adds to capital costs.

SUMMARY OF THE INVENTION

The present invention provides materials and methods for preparing enantiomerically enriched γ-amino acids (Formula 1) such as pregabalin (Formula 9). The method of the present invention involves a kinetic resolution of a racemic cyano diester intermediate (Formula 4 or Formula 12) using an enzyme that is adapted to enantioselectively hydrolyze an ester moiety of the intermediate. The resulting dicarboxylic acid monoester (Formula 3 or Formula 11), which is substantially enantiopure, undergoes further reaction to yield the desired enantiomerically-enriched γ-amino acids (Formula 1 or Formula 9). The unreacted enantiomer (Formula 5 or Formula 13) from the kinetic resolution can be reused in the enzymatic resolution following racemization, thereby improving overall yield.

The claimed method offers significant advantages over existing processes for preparing enantiomerically-enriched γ-amino acids (Formula 1 and Formula 9). For example, the optically-active γ-amino acids can be prepared without using chiral auxiliaries or proprietary hydrogenation catalysts, which should lead to lower unit costs. Since enzymatic processes can be carried out at room temperature and at atmospheric pressure, the claimed methods should help minimize scheduling conflicts arising from the use of specialized equipment capable of handling high pressures and low temperatures. As noted in the examples, the present invention can be used to prepare pregabalin starting from a racemic cyano-substituted diester (Formula 12) in good yield (26% to 31%) after a single batch recycle of the unreacted enantiomer (Formula 13). This translates into about a 50% savings in cost of goods over the malonate method described above.

One aspect of the present invention provides a method of making a compound of Formula 1,

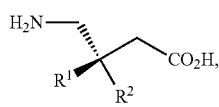

1 or a pharmaceutically acceptable complex, salt, solvate or hydrate thereof, in which $R^1$ and $R^2$ are different and are each independently selected from hydrogen atom, $C_{1-12}$ alkyl, $C_{3-12}$ cycloalkyl, and substituted $C_{3-12}$ cycloalkyl, the method comprising:

(a) reacting a compound of Formula 2,

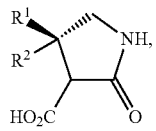

2 or a salt thereof, with an acid and water to yield the compound of Formula 1 or a salt thereof; and (b) optionally converting the compound of Formula 1 or a salt thereof into a pharmaceutically acceptable complex, salt, solvate or hydrate, wherein $R^1$ and $R^2$ in Formula 2 are as defined in Formula 1.

Another aspect of the present invention provides a method of making a compound of Formula 1, above, the method comprising:

(a) reducing a cyano moiety of a compound of Formula 6,

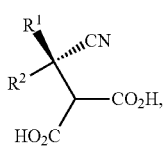

6 or a salt thereof, to yield a compound of Formula 7,

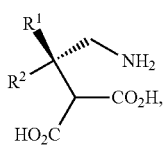

7 or a salt thereof;

(b) decarboxylating the compound of Formula 7 or a salt thereof to yield the compound of Formula 1 or a salt thereof; and (c) optionally converting the compound of Formula 1 or a salt thereof into a pharmaceutically acceptable complex, salt, solvate or hydrate, wherein $R^1$ and $R^2$ in Formula 6 and in Formula 7 are as defined above in Formula 1.

The compound of Formula 6, above, may be prepared by hydrolyzing a compound of Formula 3,

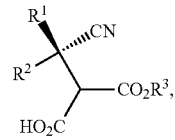

3 or a salt thereof, wherein $R^1$ and $R^2$ in Formula 3 are as defined above in Formula 1, and $R^3$ is $C_{1-12}$ alkyl, $C_{3-12}$ cycloalkyl, or aryl-$C_{1-6}$ alkyl.

An additional aspect of the present invention provides method of making a compound of Formula 1, above, the method comprising:

(a) reducing a cyano moiety of a compound of Formula 8,

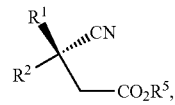

8 or a salt thereof, to yield the compound of Formula 1 or a salt thereof; and (b) optionally converting the compound of Formula 1 or a salt thereof into a pharmaceutically acceptable complex, salt, solvate or hydrate, wherein $R^1$ and $R^2$ in Formula 8 are as defined above in Formula 1, and $R^5$ in Formula 8 is hydrogen atom, $C_{1-12}$ alkyl, $C_{3-12}$ cycloalkyl, or aryl-$C_{1-6}$ alkyl.

The compound of Formula 8 may be prepared by decarboxylating a compound of Formula 3, above, or a salt thereof, or by hydrolyzing and decarboxylating the compound of Formula 3 or a salt thereof, to yield the compound of Formula 8 or a salt thereof.

A further aspect of the present invention provides a method of making the compound of Formula 3, above, or a salt thereof, the method comprising:

(a) contacting a compound of Formula 4,

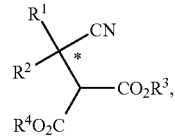

4 with an enzyme to yield the compound of Formula 3 and a compound of Formula 5,

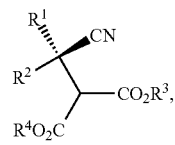

5 wherein the enzyme is adapted to enantioselectively hydrolyze the compound of Formula 4 to the compound of Formula 3 or a salt thereof;

(b) isolating the compound of Formula 3 or a salt thereof; and (c) optionally racemizing the compound of Formula 5 to yield the compound of Formula 4, wherein $R^1$, $R^2$, and $R^3$ in Formula 4 and Formula 5 are as defined above in Formula 1 and Formula 3; and $R^4$ in Formula 4 and Formula 5 is the same as or different than $R^3$ and is $C_{1-12}$ alkyl, $C_{3-12}$ cycloalkyl, or aryl-$C_{1-6}$ alkyl.

Any number of enzymes may be used to enantioselectively hydrolyze the compound of Formula 4 to the compound of Formula 3 or a salt thereof. Useful enzymes include lipases, such as those derived from *Thermomyces lanuginosus*.

Another aspect of the present invention provides compounds represented by Formula 2, above, including complexes, salts, solvates or hydrates thereof, provided that when one of the substituents represented by $R^1$ or $R^2$ in Formula 2 is hydrogen, the other substituent is not $C_{1-3}$ alkyl or $C_5$ alkyl.

An additional aspect of the present invention provides compounds of Formula 27,

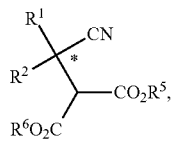

27 including complexes, salts, solvates or hydrates thereof, wherein $R^1$ and $R^2$ are different and are each independently selected from hydrogen atom, $C_{1-12}$ alkyl, $C_{3-12}$ cycloalkyl, and substituted $C_{3-12}$ cycloalkyl, provided that when one of the substituents represented by $R^1$ or $R^2$ is a hydrogen atom, the other substituent is not methyl; and $R^5$ and $R^6$ are independently selected from hydrogen atom, $C_{1-12}$ alkyl, $C_{3-12}$ cycloalkyl, or aryl-$C_{1-6}$ alkyl, provided that $R^5$ and $R^6$ are different if not hydrogen atoms.

Compounds of Formula 27 include those represented by Formula 3, Formula 4, Formula 5, Formula 6, and Formula 7, above, including their complexes, salts, solvates or hydrates. Useful compounds of Formula 2-7 and 27 include those in which $R^1$ is a hydrogen atom and $R^2$ is isobutyl.

A further aspect of the present invention provides a method of making a compound of Formula 9,

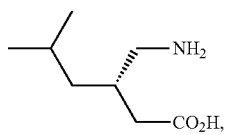

9 or a pharmaceutically acceptable complex, salt, solvate or hydrate thereof, the method comprising:

(a) reacting a compound of Formula 10,

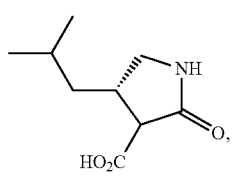

10 or a salt thereof, with an acid and water to yield the compound of Formula 9 or a salt thereof; and (b) optionally converting the compound of Formula 9 or a salt thereof into a pharmaceutically acceptable complex, salt, solvate or hydrate.

The compound of Formula 10 or a salt thereof may be prepared by reducing a cyano moiety of a compound of Formula 11,

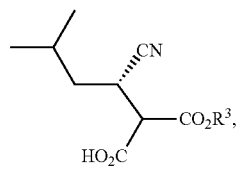

11 or a salt thereof, wherein $R^3$ is as defined above in Formula 3.

Another aspect of the present invention provides a method of making a compound of Formula 9, above, or a pharmaceutically acceptable complex, salt, solvate or hydrate thereof, the method comprising:

(a) reducing a cyano moiety of a compound of Formula 14,

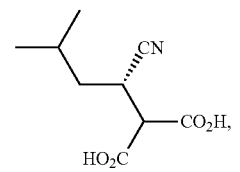

14 or a salt thereof, to yield a compound of Formula 15,

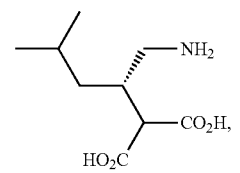

15 or a salt thereof;

(b) decarboxylating the compound of Formula 15 or a salt thereof to yield the compound of Formula 9 or a salt thereof; and (c) optionally converting the compound of Formula 9 or a salt thereof into a pharmaceutically acceptable complex, salt, solvate or hydrate.

The compound of Formula 14, above, may be prepared by hydrolyzing a compound of Formula 11,

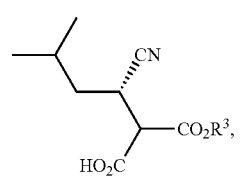

11 or salt thereof, wherein $R^3$ in Formula 11 is as defined above in Formula 3.

An additional aspect of the present invention provides a method of making a compound of Formula 9, above, or a pharmaceutically acceptable complex, salt, solvate or hydrate thereof, the method comprising:

(a) reducing a cyano moiety of a compound of Formula 16,

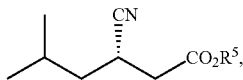

16 or a salt thereof, to yield the compound of Formula 9 or a salt thereof; and (b) optionally converting the compound of Formula 9 or a salt thereof into a pharmaceutically acceptable complex, salt, solvate or hydrate, wherein $R^5$ in Formula 16 is as defined above in Formula 8.

The compound of Formula 16 may be prepared by decarboxylating (e.g., by heating) the compound of Formula 11, above, or a salt thereof, or by hydrolyzing and decarboxylating the compound of Formula 11 or a salt thereof.

A further aspect of the present invention provides a method of making the compound of Formula 11, above, or a salt thereof, the method comprising:

(a) contacting a compound of Formula 12,

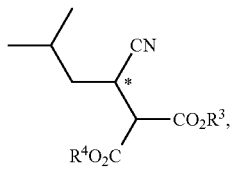

12 with an enzyme to yield the compound of Formula 11 and a compound of Formula 13,

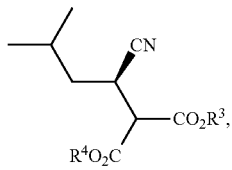

13 wherein the enzyme is adapted to enantioselectively hydrolyze the compound of Formula 12 to the compound of Formula 11 or a salt thereof;

(b) isolating the compound of Formula 11 or its salts thereof; and (c) optionally racemizing the compound of Formula 13 to yield the compound of Formula 12, wherein $R^3$ in Formula 12 and Formula 13 is as defined above in Formula 3; and $R^4$ in Formula 12 and Formula 13 is as defined above in Formula 4 and 5.

In the method for preparing the compound of Formula 11, the corresponding salts of the compound of Formula 11 include those selected from alkali metal salts, such as potassium salt; primary amine salts, such as a t-butyl amine salt; and secondary amine salts. Furthermore, useful enzymes include lipases, such as those derived from *Thermomyces lanuginosus*.

Another aspect of the present invention provides a compound selected from:
3-cyano-2-ethoxycarbonyl-5-methyl-hexanoic acid,
(3S)-3-cyano-2-ethoxycarbonyl-5-methyl-hexanoic acid,
(2S,3S)-3-cyano-2-ethoxycarbonyl-5-methyl-hexanoic acid,
(2R,3S)-3-cyano-2-ethoxycarbonyl-5-methyl-hexanoic acid,
3-cyano-2-ethoxycarbonyl-5-methyl-hexanoic acid ethyl ester,
(R)-3-cyano-2-ethoxycarbonyl-5-methyl-hexanoic acid ethyl ester,
4-isobutyl-2-oxo-pyrrolidine-3-carboxylic acid,
(S)-4-isobutyl-2-oxo-pyrrolidine-3-carboxylic acid,
3-cyano-2-carboxy-5-methyl-hexanoic acid,
(S)-3-cyano-2-carboxy-5-methyl-hexanoic acid,
3-aminomethyl-2-carboxy-5-methyl-hexanoic acid, and
(S)-3-aminomethyl-2-carboxy-5-methyl-hexanoic acid,
including complexes, salts, solvates, and hydrates thereof and opposite enantiomers thereof.

The present invention includes all complexes and salts, whether pharmaceutically acceptable or not, solvates, hydrates, and polymorphic forms of the disclosed compounds. Certain compounds may contain an alkenyl or cyclic group, so that cis/trans (or Z/E) stereoisomers are possible, or may contain a keto or oxime group, so that tautomerism may occur. In such cases, the present invention generally includes all Z/E isomers and tautomeric forms, whether they are pure, substantially pure, or mixtures.

DETAILED DESCRIPTION

Definitions and Abbreviations

Figure 1:
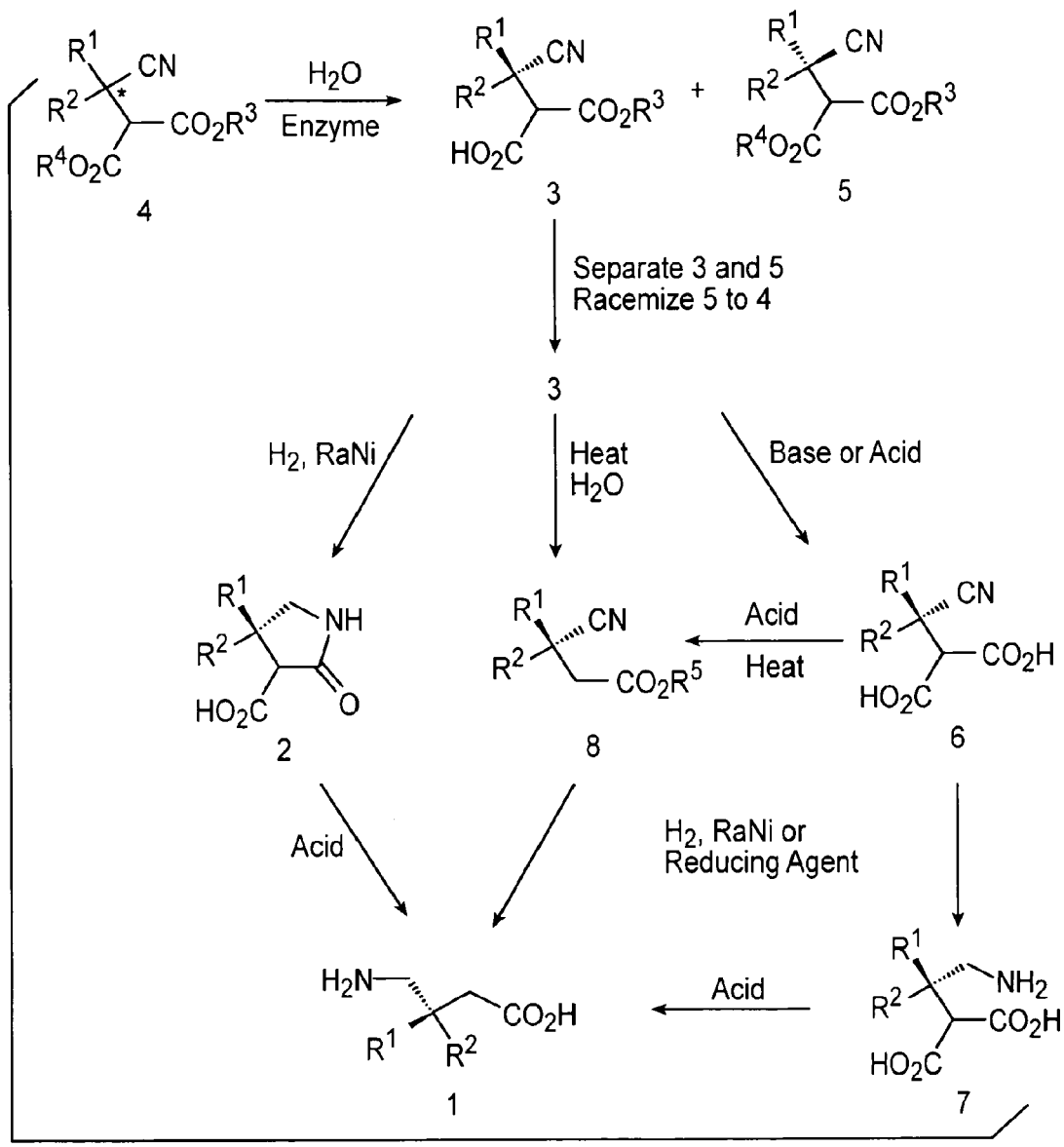
FIG. 1 depicts a scheme for preparing enantiomerically-enriched γ-amino acids (Formula 1).

Unless otherwise indicated, this disclosure uses definitions provided below. Some of the definitions and formulae may include a dash ("-") to indicate a bond between atoms or a point of attachment to a named or unnamed atom or group of atoms. Other definitions and formulae may include an equal sign ("=") or an identity symbol ("≡") to indicate a double bond or a triple bond, respectively. Certain formulae may also include one or more asterisks ("*") to indicate stereogenic (asymmetric or chiral) centers, although the absence of an asterisk does not indicate that the compound lacks a stereocenter. Such formulae may refer to the racemate or to individual enantiomers or to individual diastereomers, which may or may not be pure or substantially pure.

"Substituted" groups are those in which one or more hydrogen atoms have been replaced with one or more non-hydrogen groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value (e.g., within the 95% confidence interval for the mean) or within ±10 percent of the indicated value, whichever is greater.

"Alkyl" refers to straight chain and branched saturated hydrocarbon groups, generally having a specified number of carbon atoms (i.e., $C_{1-6}$ alkyl refers to an alkyl group having 1, 2, 3, 4, 5, or 6 carbon atoms and $C_{1-12}$ alkyl refers to an alkyl group having 1, 2, 3, 4, 5, 6, 7, 8, 9, 10, 11, or 12 carbon atoms). Examples of alkyl groups include, without limitation, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkenyl" refers to straight chain and branched hydrocarbon groups having one or more unsaturated carbon-carbon bonds, and generally having a specified number of carbon atoms. Examples of alkenyl groups include, without limitation, ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include, without limitation, ethynyl, 1-propyn-1-yl, 2-propyn-1-yl, 1-butyn-1-yl, 3-butyn-1-yl, 3-butyn-2-yl, 2-butyn-1-yl, and the like.

"Alkanoyl" and "alkanoylamino" refer, respectively, to alkyl-C(O)— and alkyl-C(O)—NH—, where alkyl is defined above, and generally includes a specified number of carbon atoms, including the carbonyl carbon. Examples of alkanoyl groups include, without limitation, formyl, acetyl, propionyl, butyryl, pentanoyl, hexanoyl, and the like.

"Alkenoyl" and "alkynoyl" refer, respectively, to alkenyl-C(O)— and alkynyl-C(O)—, where alkenyl and alkynyl are defined above. References to alkenoyl and alkynoyl generally include a specified number of carbon atoms, excluding the carbonyl carbon. Examples of alkenoyl groups include, without limitation, propenoyl, 2-methylpropenoyl, 2-butenoyl, 3-butenoyl, 2-methyl-2-butenoyl, 2-methyl-3-butenoyl, 3-methyl-3-butenoyl, 2-pentenoyl, 3-pentenoyl, 4-pentenoyl, and the like. Examples of alkynoyl groups include, without limitation, propynoyl, 2-butynoyl, 3-butynoyl, 2-pentynoyl, 3-pentynoyl, 4-pentynoyl, and the like.

"Alkoxy," "alkoxycarbonyl," and "alkoxycarbonylamino," refer, respectively, to alkyl-O—, alkenyl-O, and alkynyl-O; to alkyl-O—C(O)—, alkenyl-O—C(O)—, alkynyl-O—C(O)—; and to alkyl-O—C(O)—NH—, alkenyl-O—C(O)—NH—, and alkynyl-O—C(O)—NH—, where alkyl, alkenyl, and alkynyl are defined above. Examples of alkoxy groups include, without limitation, methoxy, ethoxy, n-propoxy, i-propoxy, n-butoxy, s-butoxy, t-butoxy, n-pentoxy, s-pentoxy, and the like. Examples of alkoxycarbonyl groups include, without limitation, methoxycarbonyl, ethoxycarbonyl, n-propoxycarbonyl, i-propoxycarbonyl, n-butoxy carbonyl, s-butoxycarbonyl, t-butoxycarbonyl, n-pentoxycarbonyl, s-pentoxycarbonyl, and the like.

"Alkylamino," "alkylaminocarbonyl," "dialkylaminocarbonyl," "alkylsulfonyl" "sulfonylaminoalkyl," and "alkylsulfonylaminocarbonyl" refer, respectively, to alkyl-NH—, alkyl-NH—C(O)—, alkyl$_2$-N—C(O)—, alkyl-S(O$_2$)—, HS(O$_2$)—NH-alkyl-, and alkyl-S(O)—NH—C(O)— where alkyl is defined above.

"Aminoalkyl" and "cyanoalkyl" refer, respectively, to NH$_2$-alkyl and N≡C-alkyl, where alkyl is defined above.

"Halo," "halogen" and "halogeno" may be used interchangeably, and refer to fluoro, chloro, bromo, and iodo.

"Haloalkyl," "haloalkenyl," "haloalkynyl," "haloalkanoyl," "haloalkenoyl," "haloalkynoyl," "haloalkoxy," and "haloalkoxycarbonyl" refer, respectively, to alkyl, alkenyl, alkynyl, alkanoyl, alkenoyl, alkynoyl, alkoxy, and alkoxycarbonyl groups substituted with one or more halogen atoms, where alkyl, alkenyl, alkynyl, alkanoyl, alkenoyl, alkynoyl, alkoxy, and alkoxycarbonyl are defined above. Examples of haloalkyl groups include, without limitation, trifluoromethyl, trichloromethyl, pentafluoroethyl, pentachloroethyl, and the like.

"Hydroxyalkyl" and "oxoalkyl" refer, respectively, to HO-alkyl and O=alkyl, where alkyl is defined above. Examples of hydroxyalkyl and oxoalkyl groups, include, without limitation, hydroxymethyl, hydroxyethyl, 3-hydroxypropyl, oxomethyl, oxoethyl, 3-oxopropyl, and the like.

"Cycloalkyl" refers to saturated monocyclic and bicyclic hydrocarbon rings, generally having a specified number of carbon atoms that comprise the ring (i.e., C$_{3-7}$ cycloalkyl refers to a cycloalkyl group having 3, 4, 5, 6 or 7 carbon atoms as ring members). The cycloalkyl may be attached to a parent group or to a substrate at any ring atom, unless such attachment would violate valence requirements. Likewise, the cycloalkyl groups may include one or more non-hydrogen substituents unless such substitution would violate valence requirements. Useful substituents include, without limitation, alkyl, alkenyl, alkynyl, haloalkyl, haloalkenyl, haloalkynyl, alkoxy, alkoxycarbonyl, alkanoyl, and halo, as defined above, and hydroxy, mercapto, nitro, and amino.

Examples of monocyclic cycloalkyl groups include, without limitation, cyclopropyl, cyclobutyl, cyclopentyl, cyclohexyl, and the like. Examples of bicyclic cycloalkyl groups include, without limitation, bicyclo[1.1.0]butyl, bicyclo[1.1.1]pentyl, bicyclo[2.1.0]pentyl, bicyclo[2.1.1]hexyl, bicyclo[3.1.0]hexyl, bicyclo[2.2.1]heptyl, bicyclo[3.2.0]heptyl, bicyclo[3.1.1]heptyl, bicyclo[4.1.0]heptyl, bicyclo[2.2.2]octyl, bicyclo[3.2.1]octyl, bicyclo[4.1.1]octyl, bicyclo[3.3.0]octyl, bicyclo[4.2.0]octyl, bicyclo[3.3.1]nonyl, bicyclo[4.2.1]nonyl, bicyclo[4.3.0]nonyl, bicyclo[3.3.2]decyl, bicyclo[4.2.2]decyl, bicyclo[4.3.1]decyl, bicyclo[4.4.0]decyl, bicyclo[3.3.3]undecyl, bicyclo[4.3.2]undecyl, bicyclo[4.3.3]dodecyl, and the like, which may be attached to a parent group or substrate at any of the ring atoms, unless such attachment would violate valence requirements.

"Cycloalkenyl" refers monocyclic and bicyclic hydrocarbon rings having one or more unsaturated carbon-carbon bonds and generally having a specified number of carbon atoms that comprise the ring (i.e., C$_{3-7}$ cycloalkenyl refers to a cycloalkenyl group having 3, 4, 5, 6 or 7 carbon atoms as ring members). The cycloalkenyl may be attached to a parent group or to a substrate at any ring atom, unless such attachment would violate valence requirements. Likewise, the cycloalkenyl groups may include one or more non-hydrogen substituents unless such substitution would violate valence requirements. Useful substituents include, without limitation, alkyl, alkenyl, alkynyl, haloalkyl, haloalkenyl, haloalkynyl, alkoxy, alkoxycarbonyl, alkanoyl, and halo, as defined above, and hydroxy, mercapto, nitro, and amino.

"Cycloalkanoyl" and "cycloalkenoyl" refer to cycloalkyl-C(O)— and cycloalkenyl-C(O)—, respectively, where cycloalkyl and cycloalkenyl are defined above. References to cycloalkanoyl and cycloalkenoyl generally include a specified number of carbon atoms, excluding the carbonyl carbon. Examples of cycloalkanoyl groups include, without limitation, cyclopropanoyl, cyclobutanoyl, cyclopentanoyl, cyclohexanoyl, cycloheptanoyl, 1-cyclobutenoyl, 2-cyclobutenoyl, 1-cyclopentenoyl, 2-cyclopentenoyl, 3-cyclopentenoyl, 1-cyclohexenoyl, 2-cyclohexenoyl, 3-cyclohexenoyl, and the like.

"Cycloalkoxy" and "cycloalkoxycarbonyl" refer, respectively, to cycloalkyl-O— and cycloalkenyl-O and to cycloalkyl-O—C(O)— and cycloalkenyl-O—C(O)—, where cycloalkyl and cycloalkenyl are defined above. References to cycloalkoxy and cycloalkoxycarbonyl generally include a specified number of carbon atoms, excluding the carbonyl carbon. Examples of cycloalkoxy groups include, without limitation, cyclopropoxy, cyclobutoxy, cyclopentoxy, cyclohexoxy, 1-cyclobutenoxy, 2-cyclobutenoxy, 1-cyclopentenoxy, 2-cyclopentenoxy, 3-cyclopentenoxy, 1-cyclohexenoxy, 2-cyclohexenoxy, 3-cyclohexenoxy, and the like. Examples of cycloalkoxycarbonyl groups include, without limitation, cyclopropoxycarbonyl, cyclobutoxycarbonyl, cyclopentoxycarbonyl, cyclohexoxycarbonyl, 1-cyclobutenoxycarbonyl, 2-cyclobutenoxycarbonyl, 1-cyclopentenoxycarbonyl, 2-cyclopentenoxycarbonyl, 3-cyclopentenoxycarbonyl, 1-cyclohexenoxycarbonyl, 2-cyclohexenoxycarbonyl, 3-cyclohexenoxycarbonyl, and the like.

"Aryl" and "arylene" refer to monovalent and divalent aromatic groups, respectively, including 5- and 6-membered monocyclic aromatic groups that contain 0 to 4 heteroatoms independently selected from nitrogen, oxygen, and sulfur. Examples of monocyclic aryl groups include, without limitation, phenyl, pyrrolyl, furanyl, thiophenyl, thiazolyl, isothiazolyl, imidazolyl, triazolyl, tetrazolyl, pyrazolyl, oxazolyl, isooxazolyl, pyridinyl, pyrazinyl, pyridazinyl, pyrimidinyl, and the like. Aryl and arylene groups also include bicyclic groups, tricyclic groups, etc., including fused 5- and 6-membered rings described above. Examples of multicyclic aryl groups include, without limitation, naphthyl, biphenyl, anthracenyl, pyrenyl, carbazolyl, benzoxazolyl, benzodioxazolyl, benzothiazolyl, benzoimidazolyl, benzothiophenyl, quinolinyl, isoquinolinyl, indolyl, benzofuranyl, purinyl, indolizinyl, and the like. They aryl and arylene groups may be attached to a parent group or to a substrate at any ring atom, unless such attachment would violate valence requirements. Likewise, aryl and arylene groups may include one or more non-hydrogen substituents unless such substitution would violate valence requirements. Useful substituents include, without limitation, alkyl, alkenyl, alkynyl, haloalkyl, haloalkenyl, haloalkynyl, cycloalkyl, cycloalkenyl, alkoxy, cycloalkoxy, alkanoyl, cycloalkanoyl, cycloalkenoyl, alkoxycarbonyl, cycloalkoxycarbonyl, and halo, as defined above, and hydroxy, mercapto, nitro, amino, and alkylamino.

"Heterocycle" and "heterocyclyl" refer to saturated, partially unsaturated, or unsaturated monocyclic or bicyclic rings having from 5 to 7 or from 7 to 11 ring members, respectively. These groups have ring members made up of carbon atoms and from 1 to 4 heteroatoms that are independently nitrogen, oxygen or sulfur, and may include any bicyclic group in which any of the above-defined monocyclic heterocycles are fused to a benzene ring. The nitrogen and sulfur heteroatoms may optionally be oxidized. The heterocyclic ring may be attached to a parent group or to a substrate at any heteroatom or carbon atom unless such attachment would violate valence requirements. Likewise, any of the carbon or nitrogen ring members may include a non-hydrogen substituent unless such substitution would violate valence requirements. Useful substituents include, without limitation, alkyl, alkenyl, alkynyl, haloalkyl, haloalkenyl, haloalkynyl, cycloalkyl, cycloalkenyl, alkoxy, cycloalkoxy, alkanoyl, cycloalkanoyl, cycloalkenoyl, alkoxycarbonyl, cycloalkoxycarbonyl, and halo, as defined above, and hydroxy, mercapto, nitro, amino, and alkylamino.

Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Heteroaryl" and "heteroarylene" refer, respectively, to monovalent and divalent heterocycles or heterocyclyl groups, as defined above, which are aromatic. Heteroaryl and heteroarylene groups represent a subset of aryl and arylene groups, respectively.

"Arylalkyl" and "heteroarylalkyl" refer, respectively, to aryl-alkyl and heteroaryl-alkyl, where aryl, heteroaryl, and alkyl are defined above. Examples include, without limitation, benzyl, fluorenylmethyl, imidazol-2-yl-methyl, and the like.

"Arylalkanoyl," "heteroarylalkanoyl," "arylalkenoyl," "heteroarylalkenoyl," "arylalkynoyl," and "heteroarylalkynoyl" refer, respectively, to aryl-alkanoyl, heteroaryl-alkanoyl, aryl-alkenoyl, heteroaryl-alkenoyl, aryl-alkynoyl, and heteroaryl-alkynoyl, where aryl, heteroaryl, alkanoyl, alkenoyl, and alkynoyl are defined above. Examples include, without limitation, benzoyl, benzylcarbonyl, fluorenoyl, fluorenylmethylcarbonyl, imidazol-2-oyl, imidazol-2-yl-methylcarbonyl, phenylethenecarbonyl, 1-phenylethenecarbonyl, 1-phenyl-propenecarbonyl, 2-phenyl-propenecarbonyl, 3-phenyl-propenecarbonyl, imidazol-2-yl-ethenecarbonyl, 1-(imidazol-2-yl)-ethenecarbonyl, 1-(imidazol-2-yl)-propenecarbonyl, 2-(imidazol-2-yl)-propenecarbonyl, 3-(imidazol-2-yl)-propenecarbonyl, phenylethynecarbonyl, phenylpropynecarbonyl, (imidazol-2-yl)-ethynecarbonyl, (imidazol-2-yl)-propynecarbonyl, and the like.

"Arylalkoxy" and "heteroarylalkoxy" refer, respectively, to aryl-alkoxy and heteroaryl-alkoxy, where aryl, heteroaryl, and alkoxy are defined above. Examples include, without limitation, benzyloxy, fluorenylmethyloxy, imidazol-2-yl-methyloxy, and the like.

"Aryloxy" and "heteroaryloxy" refer, respectively, to aryl-O— and heteroaryl-O—, where aryl and heteroaryl are defined above. Examples include, without limitation, phenoxy, imidazol-2-yloxy, and the like.

"Aryloxycarbonyl," "heteroaryloxycarbonyl," "arylalkoxycarbonyl," and "heteroarylalkoxycarbonyl" refer, respectively, to aryloxy-C(O)—, heteroaryloxy-C(O)—, arylalkoxy-C(O)—, and heteroarylalkoxy-C(O)—, where aryloxy, heteroaryloxy, arylalkoxy, and heteroarylalkoxy are defined above. Examples include, without limitation, phenoxycarbonyl, imidazol-2-yloxycarbonyl, benzyloxycarbonyl, fluorenylmethyloxycarbonyl, imidazol-2-yl-methyloxycarbonyl, and the like.

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Enantiomeric excess" or "ee" is a measure, for a given sample, of the excess of one enantiomer over a racemic sample of a chiral compound and is expressed as a percentage. Enantiomeric excess is defined as 100×(er−1)/(er+1), where "er" is the ratio of the more abundant enantiomer to the less abundant enantiomer.

"Diastereomeric excess" or "de" is a measure, for a given sample, of the excess of one diastereomer over a sample having equal amounts of diastereomers and is expressed as a percentage. Diastereomeric excess is defined as 100×(dr−1)/(dr+1), where "dr" is the ratio of a more abundant diastereomer to a less abundant diastereomer.

"Stereoselective," "enantioselective," "diastereoselective," and variants thereof, refer to a given process (e.g., ester hydrolysis, hydrogenation, hydroformylation, palladium coupling, hydrosilation, hydrocyanation, olefin metathesis, hydroacylation, allylamine isomerization, etc.) that yields more of one stereoisomer, enantiomer, or diastereoisomer than of another, respectively.

"High level of stereoselectivity," "high level of enantioselectivity," "high level of diastereoselectivity," and variants thereof, refer to a given process that yields products having an excess of one stereoisomer, enantiomer, or diastereoisomer, which comprises at least about 90% of the products. For a pair of enantiomers or diastereomers, a high level of enantioselectivity or diastereoselectivity would correspond to an ee or de of at least about 80%.

"Stereoisomerically enriched," "enantiomerically enriched," "diastereomerically enriched," and variants thereof, refer, respectively, to a sample of a compound that has more of one stereoisomer, enantiomer or diastereomer than another. The degree of enrichment may be measured by % of total product, or for a pair of enantiomers or diastereomers, by ee or de.

"Substantially pure stereoisomer," "substantially pure enantiomer," "substantially pure diastereomer," and variants thereof, refer, respectively, to a sample containing a stereoisomer, enantiomer, or diastereomer, which comprises at least about 95% of the sample. For pairs of enantiomers and diastereomers, a substantially pure enantiomer or diastereomer would correspond to samples having an ee or de of about 90% or greater.

A "pure stereoisomer," "pure enantiomer," "pure diastereomer," and variants thereof, refer, respectively, to a sample containing a stereoisomer, enantiomer, or diastereomer, which comprises at least about 99.5% of the sample. For pairs of enantiomers and diastereomers, a pure enantiomer or pure diastereomer would correspond to samples having an ee or de of about 99% or greater.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomers" of a specified compound refer to the opposite enantiomer of the compound and to any diastereoisomers or geometric isomers (Z/E) of the compound. For example, if the specified compound has S,R,Z stereochemical configuration, its stereoisomers would include its opposite enantiomer having R,S,Z configuration, its diastereomers having S,S,Z configuration and R,R,Z configuration, and its geometric isomers having S,R,E configuration, R,S,E configuration, S,S,E configuration, and R,R,E configuration.

"Enantioselectivity value" or "E" refers to the ratio of specificity constants for each enantiomer of a compound undergoing chemical reaction or conversion and may be calculated (for the S-enantiomer) from the expression, $$E = \frac{K_S/K_{SM}}{K_R/K_{RM}} = \frac{\ln[1-\chi(1+ee_p)]}{\ln[1-\chi(1-ee_p)]} = \frac{\ln[1-\chi(1-ee_s)]}{\ln[1-\chi(1+ee_s)]},$$

where $K_S$ and $K_R$ are the 1st order rate constants for the conversion of the S- and R-enantiomers, respectively; $K_{SM}$ and $K_{RM}$ are the Michaelis constants for the S- and R-enantiomers, respectively; $\chi$ is the fractional conversion of the substrate; $ee_p$ and $ee_s$ are the enantiomeric excess of the product and substrate (reactant), respectively.

"Lipase Unit" or "LU" refers to the amount of enzyme (in g) that liberates 1 µmol of titratable butyric acid/min when contacted with tributyrin and an emulsifier (gum arabic) at 30° C. and pH 7.

"Solvate" refers to a molecular complex comprising a disclosed or claimed compound and a stoichiometric or non-stoichiometric amount of one or more solvent molecules (e.g., EtOH).

"Hydrate" refers to a solvate comprising a disclosed or claimed compound and a stoichiometric or non-stoichiometric amount of water.

"Pharmaceutically acceptable complexes, salts, solvates, or hydrates" refers to complexes, acid or base addition salts, solvates or hydrates of claimed and disclosed compounds, which are within the scope of sound medical judgment, suitable for use in contact with the tissues of patients without undue toxicity, irritation, allergic response, and the like, commensurate with a reasonable benefit/risk ratio, and effective for their intended use.

"Pre-catalyst" or "catalyst precursor" refers to a compound or set of compounds that are converted into a catalyst prior to use.

"Treating" refers to reversing, alleviating, inhibiting the progress of, or preventing a disorder or condition to which such term applies, or to preventing one or more symptoms of such disorder or condition.

"Treatment" refers to the act of "treating," as defined immediately above.

Table 1 lists abbreviations used throughout the specification.

TABLE 1

List of Abbreviations

| Abbreviation | Description |
| --- | --- |
| Ac | Acetyl |
| ACN | acetonitrile |
| AcNH | acetylamino |
| aq | aqueous |
| BES | N,N-bis(2-hydroxyethyl)-2-aminoethanesulfonic acid |
| BICINE | N,N-bis(2-hydroxyethyl)glycine |
| Bn | benzyl |
| Bu | Butyl |
| n-BuLi | normal-butyl lithium |
| Bu$_4$NBr | tetrabutylammonium bromide |
| t-BuNH$_2$ | tertiary-butylamine |
| t-BuOK | potassium tertiary butyl oxide |
| t-BuOMe | tertiary butyl methyl ether |
| t-BuONa | sodium tertiary butyl oxide |
| CBz | benzyloxycarbonyl |
| χ | fractional conversion |
| COD | 1,5-cyclooctadiene |
| DABCO | 1,4-diazabicyclo[2.2.2]octane |
| DBU | 1,8-diazabicyclo[5.4.0]undec-7-ene |
| DEAD | diethylazodicarboxylate |
| DIPEA | diisopropylethylamine (Hünig's Base) |
| DMAP | 4-dimethylaminopyridine |
| DMF | dimethylformamide |
| DMSO | dimethylsulfoxide |
| E | Enantioselectivity value or ratio of specificity constants for each enantiomer of a compound undergoing chemical reaction or conversion |
| ee (ee$_p$ or ee$_s$) | enantiomeric excess (of product or reactant) |
| eq | equivalents |
| er | enantiomeric ratio |
| Et | ethyl |
| Et$_3$N | triethylamine |
| Et$_2$NH | diethylamine |
| EtOH | ethyl alcohol |
| EtOAc | ethyl acetate |
| h, min, s, d | hours, minutes, seconds, days |
| HEPES | 4-(2-hydroxyethyl)piperazine-1-ethanesulfonic acid |
| HOAc | acetic acid |
| HPLC | high performance liquid chromatography |
| IAcOEt | ethyl iodoacetate |
| IPA | isopropanol |
| K$_S$, K$_S$ | 1st order rate constant for S- or R-enantiomer |
| K$_{SM}$, K$_{RM}$ | Michaelis constant for S- or R-enantiomer |
| LC/MS | liquid chromatography mass spectrometry |
| LDA | Lithium diisopropylamide |
| LiHMDS | Lithium hexamethyldisilazide |
| LTMP | Lithium tetramethylpiperidide |
| LU | lipase unit |
| Me | methyl |
| MeCl$_2$ | methylene chloride |
| (R,R)-Me-DUPHOS | (—)-1,2-bis((2R,5R)-2,5-dimethyl-phospholano)benzene |
| MeI | methyl iodide |
| MeONa | sodium methoxide |
| MeOH | methyl alcohol |
| MES | 2-morpholinoethanesulfonic acid |
| MOPS | 3-(N-morpholino)propanesulfonic acid |
| Mpa | mega Pascals |
| Ms | Mesyl or methylsulfonyl |
| MTBE | methyl tertiary butyl ether |
| NMP | N-methylpyrrolidone |
| OTf$^-$ | triflate (trifluoro-methanesulfonic acid anion) |
| Ph | phenyl |
| Ph$_3$P | triphenylphosphine |
| Ph$_3$As | triphenylarsine |
| PIPES | piperazine-1,4-bis(2-ethanesulfonic acid) |
| RaNi | Raney nickel |
| RI | refractive index |
| RT | room temperature (approximately 20° C.-25° C.) |
| s/c | substrate-to-catalyst molar ratio |
| sp | species |

TABLE 1-continued

List of Abbreviations

| Abbreviation | Description |
| --- | --- |
| TAPS | N-[tris(hydroxymethyl)methyl]-3-aminopropanesulfonic acid |
| TES | N-[tris(hydroxymethyl)methyl]-2-aminoethanesulfonic acid |
| Tf | trifluoromethanesulfonyl (triflyl) |
| TFA | trifluoroacetic acid |
| THF | tetrahydrofuran |
| TLC | thin-layer chromatography |
| TMEDA | N,N,N',N'-tetramethyl-1,2-ethylenediamine |
| TRICINE | N-[tris(hydroxymethyl)methyl]glycine |
| Tris buffer | tris(hydroxymethyl)aminomethane buffer |
| TRITON B | benzyltrimethylammonium hydroxide |
| TRIZMA ® | 2-amino-2-(hydroxymethyl)-1,3-propanediol |
| Ts | tosyl or p-toluenesulfonyl |
| p-TSA | para-toluene sulfonic acid |
| v/v | volume percent |
| w/w | weight (mass) percent |

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and the like, see T. W. Greene and P. G. Wuts, *Protecting Groups in Organic Chemistry* (1999) and P. Kocienski, *Protective Groups* (2000), which are herein incorporated by reference in their entirety for all purposes.

In addition, some of the schemes and examples below may omit details of common reactions, including oxidations, reductions, and so on, which are known to persons of ordinary skill in the art of organic chemistry. The details of such reactions can be found in a number of treatises, including Richard Larock, *Comprehensive Organic Transformations* (1999), and the multi-volume series edited by Michael B. Smith and others, *Compendium of Organic Synthetic Methods* (1974-2003). Generally, starting materials and reagents may be obtained from commercial sources or may be prepared from literature sources.

Generally, the chemical transformations described throughout the specification may be carried out using substantially stoichiometric amounts of reactants, though certain reactions may benefit from using an excess of one or more of the reactants. Additionally, many of the reactions disclosed throughout the specification, including the enantioselective hydrolysis of the racemic diester (Formula 4) described in detail below, may be carried out at about RT, but particular reactions may require the use of higher or lower temperatures, depending on reaction kinetics, yields, and the like. Furthermore, many of the chemical transformations may employ one or more compatible solvents, which may influence the reaction rate and yield. Depending on the nature of the reactants, the one or more solvents may be polar protic solvents, polar aprotic solvents, non-polar solvents, or some combination. Any references in the disclosure to a concentration range, a temperature range, a pH range, a catalyst loading range, and so on, whether expressly using the word "range" or not, include the indicated endpoints.

The present invention provides materials and methods for preparing optically active γ-amino acids (Formula 1) including pharmaceutically acceptable salts, esters, amides, or prodrugs thereof. The compounds of Formula 1 include substituents $R^1$ and $R^2$, which are defined above. Useful compounds of Formula 1 thus include those in which $R^1$ is a hydrogen atom and $R^2$ is $C_{1-12}$ alkyl, $C_{3-12}$ cycloalkyl, or substituted $C_{3-12}$ cycloalkyl, or those in which $R^2$ is a hydrogen atom and $R^1$ is $C_{1-12}$ alkyl, $C_{3-12}$ cycloalkyl, or substituted $C_{3-12}$ cycloalkyl. Particularly useful compounds of Formula 1 include those in which $R^1$ is a hydrogen atom and $R^2$ is $C_{1-6}$ alkyl or $C_{3-7}$ cycloalkyl, or those in which $R^2$ is a hydrogen atom and $R^1$ is $C_{1-6}$ alkyl or $C_{3-7}$ cycloalkyl. Especially useful compounds of Formula 1 include those in which $R^1$ is a hydrogen atom and $R^2$ is $C_{1-4}$ alkyl, such as pregabalin (Formula 9).

FIG. 1 shows a process for preparing optically active γ-amino acids (Formula 1). The process includes the step of contacting or combining a reaction mixture, which is comprised of a cyano-substituted diester (Formula 4) and water, with an enzyme to yield a product mixture that includes an optically active dicarboxylic acid monoester (Formula 3) and an optically-active diester (Formula 5). The cyano-substituted diester (Formula 4) has a stereogenic center, which is denoted by an asterisk ("*"), and as described below, may be prepared in accordance with a reaction scheme shown in FIG. 2. Prior to contacting the enzyme, the cyano-substituted diester (Formula 4) typically comprises a racemic (equimolar) mixture of the diester of Formula 5 and its opposite enantiomer. Substituents $R^1$, $R^2$, and $R^3$ in Formula 3, Formula 4, and Formula 5, and substituent $R^4$ in Formula 4 and Formula 5 are as defined above in connection with Formula 1. Generally, and unless stated differently, when a particular substituent identifier ($R^1$, $R^2$, $R^3$, etc.) is defined for the first time in connection with a formula, the same substituent identifier used in a subsequent formula will have the same meaning as in the earlier formula.

The enzyme (or biocatalyst) may be any protein that, while having little or no effect on the compound of Formula 5, will catalyze the hydrolysis of its opposite enantiomer to yield the dicarboxylic acid monoester (Formula 3). Useful enzymes for enantioselectively hydrolyzing the compound of Formula 4 to Formula 3 may thus include hydrolases, including lipases, certain proteases, and other enantioselective esterases. Such enzymes may be obtained from a variety of natural sources, including animal organs and microorganisms. See, e.g., Table 2 for a non-limiting list of commercially available hydrolases.

TABLE 2

Commercially Available Hydrolases

| Enzyme | Trade name |
| --- | --- |
| Porcine Pancreatic Lipase | Altus03 |
| CAL-A, lyophilized | Altus11 |
| Candida lipolytica Lipase | Altus12 |
| CAL-B, lyophilized | Altus13 |
| Geotrichum candidum Lipase | Altus28 |
| Pseudomonas aroginosa Lipase | Altus50 |
| Aspergillus niger Lipase | Amano Lipase A |
| Pseudomonas cepacia Lipase | Amano Lipase AH |
| Pseudomonas fluorescens Lipase | Amano Lipase AK |
| Candida rugosa Lipase | Amano Lipase AY |
| Rhizopus delemar Lipase | Amano Lipase D |
| Rhizopus oryzae Lipase | Amano Lipase F |
| Penicillium camembertii Lipase | Amano Lipase G |
| Mucor javanicus Lipase | Amano Lipase M |
| Pseudomonas cepacia Lipase | Amano Lipase PS |
| Penicillium roqueforti Lipase | Amano Lipase R |
| Aspergillus sp. Protease | BioCatalytics101 |
| Pseudomonas sp. Lipase | BioCatalytics103 |

TABLE 2-continued

Commercially Available Hydrolases

| Enzyme | Trade name |
| --- | --- |
| Fungal Lipase | BioCatalytics105 |
| Microbial, lyophilized Lipase | BioCatalytics108 |
| CAL-B, lyophilized | BioCatalytics110 |
| Candida sp., lyophilized | BioCatalytics111 |
| CAL-A, lyophilized | BioCatalytics112 |
| Thermomyces sp. Lipase | BioCatalytics115 |
| Alcaligines sp., lyophilized Lipase | BioCatalytics117 |
| Chromobacterium viscosum Lipase | Altus26 |
| CAL-B, L2 Sol | Chriazyme L2 Sol |
| Candida utilis Lipase | Fluka6 |
| Rhizopus niveus Lipase | Sigma L8 |
| Pseudomonas sp. Lipoprotein Lipase | Sigma L13 |
| Thermomuces lanuginosus Lipase | Sigma L9 Lipolase |
| Thermomuces lanuginosus Lipase | Sigma L10 Novo871 |
| Rhizomucor miehei Lipase | Sigma L6 Palatase |
| Pseudomonas species Lipase | Sigma L14 Type XIII |
| Wheat Germ Lipase | Sigma L11 |
| Rhizopus arrhizus Lipase | Sigma L7 Type XI |
| Pancreatic Lipase 250 | Valley Research V1 |
| Trypsin Protease | Altus33 |
| Chymopapain Protease | Altus38 |
| Bromelain Protease | Altus40 |
| Aspergillus niger Protease | Altus41 |
| Aspergillus oryzae Protease | Altus42 |
| Penicillium sp. Protease | Altus43 |
| Aspergillus sp. Protease | Altus45 |
| Renin Calf Stomach Protease | Sigma P24 |
| Subtilisin Carlsberg Protease | Altus10 |
| Bacillus lentus Protease | Altus53 |
| Aspergillus niger Protease | Amano Acid Protease A |
| Rhizopus niveus Protease | Amano Acid Protease II |
| Rhizopus niveus Protease | Amano Newlase F |
| Rhizopus oryzae Protease | Amano Peptidase R |
| Bacillus subtilis Protease | Amano Proleather FGF |
| Aspergillus oryzae Protease | Amano Protease A |
| Aspergillus oryzae Protease | Amano Protease M |
| Bacillus subtilis Protease | Amano Protease N |
| Aspergillus melleus Protease | Amano Protease P |
| Bacillus stearothermophilus Protease | Amano Protease SG |
| Pig Liver Esterase, lyophilized | BioCat Chirazyme E1 |
| Pig Liver Esterase, lyophilized | BioCat Chirazyme E2 |
| Streptomyces sp. Proteases | BioCatalytics118 |
| Tritirachium album Protease | Fluka P6 Proteinase K |
| Bovine Pancreas Protease | Sigma P18 alpha chymotrypsin I |
| Streptomyces griseus Protease | Sigma P16 Bacterial |
| Bovine Pancreas Protease | Sigma P21 Beta chymotrypsin |
| Clostridium histolyticum Protease | Sigma P13 Clostripain |
| Bovine Intestine Protease | Sigma P17 Enteropeptidase |
| Porcine Intestine Protease | Sigma P25 Enteropeptidase |
| Bacillus sp. Protease | Sigma P8 Esperase |
| Aspergillus oryzae Protease | Sigma P1 Flavourzyme |
| Bacillus amyloliquefaciens Protease | Sigma P5 Neutrase |
| Carica papaya Protease | Sigma P12 Papain |
| Bacillus thermoproteolyticus rokko | Sigma P10 Protease |
| Pyrococcus furiosis Protease | Sigma P14 Protease S |
| Bacillus sp. Protease | Sigma P9 Savinase |
| Bovine Pancreas Protease | Sigma P19 Type 1 (crude) |
| Bacillus polymyxa Protease | Sigma P7 Type IX |
| Bacillus licheniformis Protease | Sigma P6 Type VIII |
| Aspergillus saitoi Protease | Sigma P3 Type XIII |
| Aspergillus sojae Protease | Sigma P4 Type XIX |
| Aspergillus oryzae Protease | Sigma P2 Type XXIII |
| Bacterial Protease | Sigma P11 Type XXIV |
| Rhizopus sp. Newlase | Sigma15 Newlase |
| Validase FP Conc. | Valley05 |
| Bromelian Conc. | Valley10 |
| Acylase from Aspergillus sp. | Amano Am1 |
| Porcine kidney Acylase | Sigma A-S2 Acylase I |
| Penicillin G Acylase | Altus06 |
| Esterase from Mucor meihei | Fluka |
| Candida rugosa Esterase | Altus31 |
| Porcine Pancreatic Elastase | Altus35 |

TABLE 2-continued

Commercially Available Hydrolases

| Enzyme | Trade name |
|---|---|
| Cholesterol Esterase | BioCatalytics |
| PLE - Ammonium Sulfate | BioCatalytics 123 |
| Rabbit Liver Esterase | Sigma ES2 |
| Cholesterol Esterase *Pseudomonas* sp. | Sigma ES4 |

As shown in the Example section, useful enzymes for the enantioselective conversion of the cyano-substituted diester (Formula 4 and Formula 12) to the desired optically active dicarboxylic acid monoester (Formula 3 and Formula 11) include lipases. Particularly useful lipases include enzymes derived from the microorganism *Thermomyces lanuginosus*, such as those available from Novo-Nordisk A/S under the trade name LIPOLASE® (CAS no. 9001-62-1). LIPOLASE® enzymes are obtained by submerged fermentation of an *Aspergillus oryzae* microorganism genetically modified with DNA from *Thermomyces lanuginosus* DSM 4109 that encodes the amino acid sequence of the lipase. LIPOLASE® 100L and LIPOLASE® 100T are available as a liquid solution and a granular solid, respectively, each having a nominal activity of 100 kLU/g. Other forms of LIPOLASE® include LIPOLASE® 50L, which has half the activity of LIPOLASE® 100L, and LIPOZYME® 100L, which has the same activity of LIPOLASE® 100L, but is food grade.

Various screening techniques may be used to identify suitable enzymes. For example, large numbers of commercially available enzymes may be screened using high throughput screening techniques described in the Example section below. Other enzymes (or microbial sources of enzymes) may be screened using enrichment isolation techniques. Such techniques typically involve the use of carbon-limited or nitrogen-limited media supplemented with an enrichment substrate, which may be the racemic substrate (Formula 4) or a structurally similar compound. Potentially useful microorganisms are selected for further investigation based on their ability to grow in media containing the enrichment substrate. These microorganisms are subsequently evaluated for their ability to enantioselectively catalyze ester hydrolysis by contacting suspensions of the microbial cells with the racemic substrate and testing for the presence of the desired optically-active dicarboxylic acid monoester (Formula 3) using analytical methods such as chiral HPLC, gas-liquid chromatography, LC/MS, and the like.

Once a microorganism having the requisite hydrolytic activity has been isolated, enzyme engineering may be employed to improve the properties of the enzyme it produces. For example, and without limitation, enzyme engineering may be used to increase the yield and the enantioselectivity of the ester hydrolysis, to broaden the temperature and pH operating ranges of the enzyme, and to improve the enzyme's tolerance to organic solvents. Useful enzyme engineering techniques include rational design methods, such as site-directed mutagenesis, and in vitro-directed evolution techniques that utilize successive rounds of random mutagenesis, gene expression, and high throughput screening to optimize desired properties. See, e.g., K. M. Koeller & C.-H. Wong, "Enzymes for chemical synthesis," *Nature* 409:232-240 (11 Jan. 2001), and references cited therein, the complete disclosures of which are herein incorporated by reference.

The enzyme may be in the form of whole microbial cells, permeabilized microbial cells, extracts of microbial cells, partially purified enzymes, purified enzymes, and the like. The enzyme may comprise a dispersion of particles having an average particle size, based on volume, of less than about 0.1 mm (fine dispersion) or of about 0.1 mm or greater (coarse dispersion). Coarse enzyme dispersions offer potential processing advantages over fine dispersions. For example, coarse enzyme particles may be used repeatedly in batch processes, or in semi-continuous or continuous processes, and may usually be separated (e.g., by filtration) from other components of the bioconversion more easily than fine dispersions of enzymes.

Useful coarse enzyme dispersions include cross-linked enzyme crystals (CLECs) and cross-linked enzyme aggregates (CLEAs), which are comprised primarily of the enzyme. Other coarse dispersions may include enzymes immobilized on or within an insoluble support. Useful solid supports include polymer matrices comprised of calcium alginate, polyacrylamide, EUPERGIT®, and other polymeric materials, as well as inorganic matrices, such as CELITE®. For a general description of CLECs and other enzyme immobilization techniques, see U.S. Pat. No. 5,618,710 to M. A. Navia & N. L. St. Clair. For a general discussion of CLEAs, including their preparation and use, see U.S. Patent Application No. 2003/0149172 to L. Cao & J. Elzinga et al. See also A. M. Anderson, *Biocat. Biotransform*, 16:181 (1998) and P. Lopez-Serrano et al., *Biotechnol. Lett.* 24:1379-83 (2002) for a discussion of the application of CLEC and CLEA technology to a lipase. The complete disclosures of the abovementioned references are herein incorporated by reference for all purposes.

The reaction mixture may comprise a single phase or may comprise multiple phases (e.g., a two- or a three-phase system). Thus, for example, the enantioselective hydrolysis shown in FIG. 1 may take place in a single aqueous phase, which contains the enzyme, the initially racemic substrate (Formula 4), the undesired optically-active diester (Formula 5), and the desired optically-active dicarboxylic acid monoester (Formula 3). Alternatively, the reaction mixture may comprise a multi-phase system that includes an aqueous phase in contact with a solid phase (e.g., enzyme or product), an aqueous phase in contact with an organic phase, or an aqueous phase in contact with an organic phase and a solid phase. For example, the enantioselective hydrolysis may be carried out in a two-phase system comprised of a solid phase, which contains the enzyme, and an aqueous phase, which contains the initially racemic substrate, the undesired optically-active diester, and the desired optically-active dicarboxylic acid monoester.

Alternatively, the enantioselective hydrolysis may be carried out in a three-phase system comprised of a solid phase, which contains the enzyme, an organic phase that initially contains the racemic substrate (Formula 4), and an aqueous phase that initially contains a small fraction of the racemic substrate. Since the desired optically-active dicarboxylic acid monoester (Formula 3) has a lower pKa than the unreacted optically-active diester (Formula 5) and therefore exhibits greater aqueous solubility, the organic phase becomes enriched in the unreacted diester while the aqueous phase becomes enriched in the desired dicarboxylic acid monoester as the reaction proceeds.

The amounts of the racemic substrate (Formula 4) and the biocatalyst used in the enantioselective hydrolysis will depend on, among other things, the properties of the particular cyano-substituted diester and enzyme. Generally, however, the reaction may employ a substrate having an initial concentration of about 0.1 M to about 3.0 M, and in many cases, having an initial concentration of about 1.5 M to about 3.0 M. Additionally, the reaction may generally employ an enzyme loading of about 1% to about 10%, and in many cases, may employ an enzyme loading of about 3% to about 4% (v/v).

The enantioselective hydrolysis may be carried out over wide ranges of temperature and pH. For example, the reaction may be carried out at a temperature of about 10° C. to a temperature of about 50° C., but is typically carried out at about RT. Such temperatures generally permit substantially full conversion (e.g., about 42% to about 50%) of the racemate (Formula 4) in a reasonable amount of time (about 2 h to about 24 h) without deactivating the enzyme. Additionally, the enantioselective hydrolysis may be carried out at a pH of about 5 to a pH of about 10, more typically at a pH of about 6 to a pH of about 9, and often at a pH of about 6.5 to a pH of about 7.5.

In the absence of pH control, the reaction mixture pH will decrease as the hydrolysis of the substrate (Formula 4) proceeds because of the formation of the dicarboxylic acid monoester (Formula 3). To compensate for this change, the hydrolysis reaction may be run with internal pH control (i.e., in the presence of a suitable buffer) or may be run with external pH control through the addition of a base. Suitable buffers include potassium phosphate, sodium phosphate, sodium acetate, ammonium acetate, calcium acetate, BES, BICINE, HEPES, MES, MOPS, PIPES, TAPS, TES, TRICINE, Tris, TRIZMA®, or other buffers having a pKa of about 6 to a pKa of about 9. The buffer concentration generally ranges from about 5 mM to about 1 mM, and typically ranges from about 50 mM to about 200 mM. Suitable bases include aqueous solutions comprised of KOH, NaOH, $NH_4OH$, etc., having concentrations ranging from about 0.5 M to about 15 M, or more typically, ranging from about 5 M to about 10 M. Other inorganic additives such as calcium acetate may also be used.

Following or during the enzymatic conversion of the racemate (Formula 4), the desired optically active dicarboxylic acid monoester (Formula 3) is isolated from the product mixture using standard techniques. For example, in the case of a single (aqueous) phase batch reaction, the product mixture may be extracted one or more times with a nonpolar organic solvent, such as hexane or heptane, which separates the desired dicarboxylic monoester (Formula 2) and the unreacted diester (Formula 5) in aqueous and organic phases, respectively. Alternatively, in the case of a multi-phase reaction employing aqueous and organic phases enriched in the desired monoester (Formula 3) and the unreacted diester (Formula 5), respectively, the monoester and diester may be separated batch-wise following reaction, or may be separated semi-continuously or continuously during the enantioselective hydrolysis.

As indicated in FIG. 1, the unreacted diester (Formula 5) may be isolated from the organic phase and racemized to yield the racemic substrate (Formula 4). The resulting racemate (Formula 4) may be recycled or combined with unconverted racemic substrate, which subsequently undergoes enzymatic conversion to Formula 3 as described above. Recycling the unreacted diester (Formula 5) increases the overall yield of the enantioselective hydrolysis above 50%, thereby increasing the atom economy of the method and lowering costs associated with disposal of the undesired enantiomers.

The treatment of the diester (Formula 5) with a base that is strong enough to abstract an acidic α-proton of the malonate moiety generally results in inversion of the stereogenic center and generation of the racemic substrate (Formula 4). Useful bases include organic bases, such as alkoxides (e.g., sodium ethoxide), linear aliphatic amines, and cyclic amines, and inorganic bases, such as KOH, NaOH, $NH_4OH$, and the like.

The reaction is carried out in a compatible solvent, including polar protic solvents, such as EtOH or aprotic polar solvents, such as MTBE. Reaction temperatures above RT typically improve the yield of the racemization process.

As shown in FIG. 1, the substantially enantiopure dicarboxylic acid monoester (Formula 3) may be converted to an optically active γ-amino acid (Formula 1) using at least three different methods. In one method, the monoester (Formula 3) is hydrolyzed in the presence of an acid catalyst or a base catalyst to yield an optically-active cyano-substituted dicarboxylic acid (Formula 6) or corresponding salt. The cyano moiety of the resulting dicarboxylic acid (or its salt) is reduced to yield an optically-active γ-amino dicarboxylic acid (Formula 7) or a corresponding salt, which is subsequently decarboxylated by treatment with an acid, by heating, or both, to yield the desired optically active γ-amino acid (Formula 1). The cyano moiety may be reduced via reaction with $H_2$ in the presence of catalytic amounts of Raney nickel, palladium, platinum, and the like, or through reaction with a reducing agent, such as $LiAlH_4$, $BH_3-Me_2S$, and the like. Useful acids for the hydrolysis and decarboxylation reactions include mineral acids, such as $HClO_4$, HI, $H_2SO_4$, HBr, HCl, and the like. Useful base catalysts for the hydrolysis reaction include various alkali and alkaline earth metal hydroxides and oxides, including LiOH, NaOH, KOH, and the like.

In another method, the dicarboxylic acid monoester (Formula 3) undergoes reductive cyclization to form an optically-active cyclic 3-carboxy-pyrrolidin-2-one (Formula 2), which is subsequently treated with an acid to yield the desired enantiomerically-enriched γ-amino acid (Formula 1). The reductive cyclization may be carried out by reacting the monoester (Formula 3) with $H_2$ in the presence of catalytic amounts of Raney nickel, palladium, platinum and the like. One or more acids may be used to hydrolyze and decarboxylate the resulting lactam acid (Formula 2), including mineral acids such as $HClO_4$, HI, $H_2SO_4$, HBr, and HCl, and organic acids such as HOAc, TFA, p-TSA, and the like. The concentration of the acids may range from about 1N to about 12 N, and the amount of the acids may range from about 1 eq to about 7 eq. The hydrolysis and decarboxylation reactions may be carried out at a temperature of about RT or higher, or at a temperature of about 60° C. or higher, or at temperature in a range of about 60° C. to about 130° C.

In a third method, the ester moiety of the dicarboxylic acid monoester (Formula 3) is first hydrolyzed to give the cyano-substituted dicarboxylic acid (Formula 6 or its salt) as described above. The resulting dicarboxylic acid (or its salt) is subsequently decarboxylated to give an optically-active cyano-substituted carboxylic acid or its salt (Formula 8 in which $R^5$ is a hydrogen atom, though $R^5$ can also be $C_{1-12}$ alkyl, $C_{3-12}$ cycloalkyl, or aryl-$C_{1-5}$ alkyl as noted below). The same conditions used to decarboxylate the lactam acid (Formula 2) or the γ-amino dicarboxylic acid (Formula 7) may be used. Instead of first hydrolyzing the ester moiety, the dicarboxylic acid monoester (Formula 3) may be first decarboxylated directly to a cyano substituted monoester (Formula 8) by heating the aqueous solution of the dicarboxylic acid monoester (as a salt) to a temperature of from about 50° C. to reflux. Krapcho conditions (DMSO/NaCl/water) may also be used. In either case, the cyano moiety of the compound of formula 8 is subsequently reduced to give the optically active γ-amino acid (Formula 1).

In addition to Raney nickel, a number of other catalysts may be used to reduce the cyano moiety of the compounds of Formula 3, 6 and 8. These include, without limitation, heterogeneous catalysts containing from about 0.1% to about 20%, and more typically, from about 1% to about 5%, by weight, of transition metals such as Ni, Pd, Pt, Rh, Re, Ru, and Ir, including oxides and combinations thereof, which are typically supported on various materials, including $Al_2O_3$, C, $CaCO_3$, $SrCO_3$, $BaSO_4$, MgO, $SiO_2$, $TiO_2$, $ZrO_2$, and the like. Many of these metals, including Pd, may be doped with an amine, sulfide, or a second metal, such as Pb, Cu, or Zn. Useful catalysts thus include palladium catalysts such as Pd/C, Pd/SrCO$_3$, Pd/Al$_2$O$_3$, Pd/MgO, Pd/CaCO$_3$, Pd/BaSO$_4$, PdO, Pd black, PdCl$_2$, and the like, containing from about 1% to about 5% Pd, based on weight. Other useful catalysts include Rh/C, Ru/C, Re/C, PtO$_2$, Rh/C, RuO$_2$, and the like.

The catalytic reduction of the cyano moiety is typically carried out in the presence of one or more polar solvents, including without limitation, water, alcohols, ethers, esters and acids, such as MeOH, EtOH, IPA, THF, EtOAc, and HOAc. The reaction may be carried out at temperatures ranging from about 5° C. to about 100° C., though reactions at RT are common. Generally, the substrate-to-catalyst ratio may range from about 1:1 to about 1000:1, based on weight, and H$_2$ pressure may range from about atmospheric pressure, 0 psig, to about 1500 psig. More typically, the substrate-to-catalyst ratios range from about 4:1 to about 20:1, and H$_2$ pressures range from about 25 psig to about 150 psig.

All of the preceding methods may be used to convert the substantially enantiopure monoester (Formula 3) to the optically active γ-amino acid (Formula 1), but each may offer certain advantages over the others. For example, following acid workup of the process employing reductive cyclization, the lactam acid (Formula 2) may be isolated and purified by extracting it into an organic solvent, whereas the cyano-substituted dicarboxylic acid (Formula 6) may be more difficult to isolate because of its comparatively higher aqueous solubility. Isolation of the lactam acid (Formula 2) reduces the carryover of water-soluble impurities into the final product mixture and permits higher reactant concentration (e.g., about 1 M to about 2 M) during hydrolysis and decarboxylation, thereby increasing process throughput. Additionally, direct decarboxylation by heating the aqueous solution of the dicarboxylic acid monoester (Formula 3) affords the cyano-monoester (Formula 8) in high enantiomeric purity. This compound can be separated from the reaction medium by extraction in an organic solvent or by direct phase separation, ensuring efficient removal of inorganic impurities by the water phase. High reaction throughput and the avoidance of strongly acidic conditions are two advantages of this approach.

Figure 2:
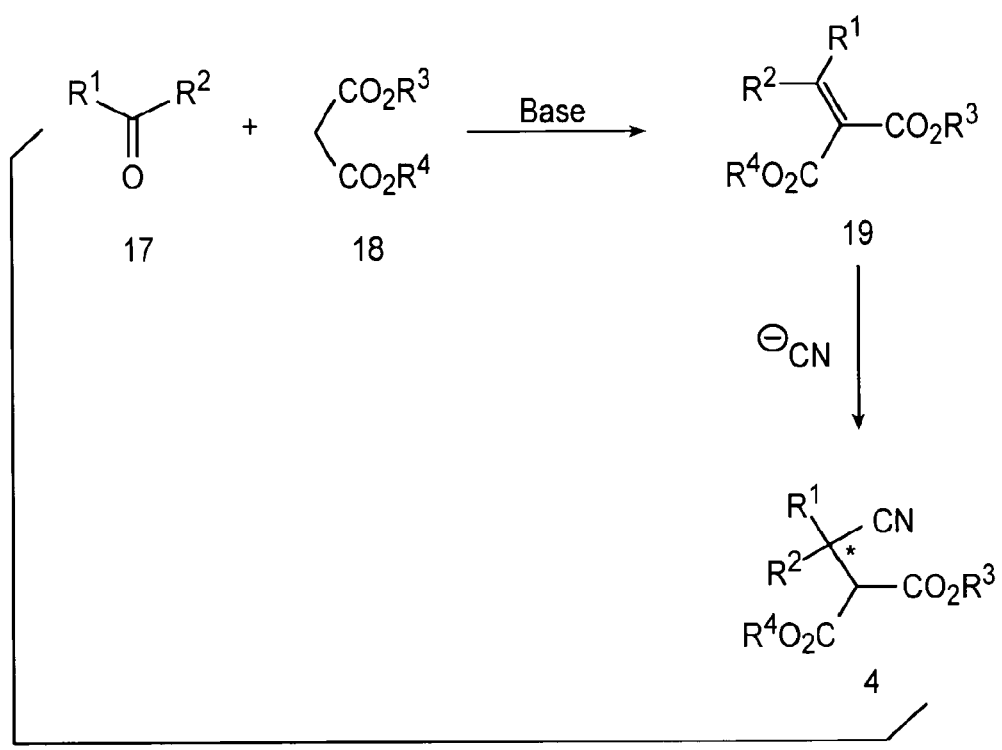
FIG. 2 depicts a scheme for preparing cyano-substituted diesters (Formula 4).

FIG. 2 illustrates a process for preparing cyano-substituted diesters (Formula 4), which may serve as substrates for the enzymatic enantioselective hydrolysis shown in FIG. 1. The process includes a crossed aldol condensation, which comprises reacting an unsymmetrical ketone or an aldehyde (Formula 17) with a malonic acid diester (Formula 18) in the presence of catalytic amounts of a base to yield an α,β-unsaturated malonic acid diester (Formula 19) in which $R^1$, $R^2$, $R^3$, and $R^4$ are as defined above in connection with Formula 1. This type of crossed aldol reaction is known as a Knoevenagel Condensation, which is described in a number of literature reviews. See, e.g., B. K. Wilk, *Tetrahedron* 53:7097-7100 (1997) and references cited therein, the complete disclosures of which are herein incorporated by reference for all purposes.

Generally, any base capable of generating an enolate ion from the malonic acid diester (Formula 18) may be used, including secondary amines, such as di-n-propylamine, di-i-propylamine, pyrrolidine, etc., and their salts. The reaction may include a carboxylic acid, such as HOAc, to neutralize the product and to minimize enolization of the unsymmetrical ketone or aldehyde (Formula 17). Reactions involving unsymmetrical ketones may also employ Lewis acids, such as titanium tetrachloride, zinc chloride, zinc acetate, and the like to facilitate reaction. The reaction is typically run in a hydrocarbon solvent under reflux conditions. Useful solvents include hexane, heptane, cyclohexane, toluene, methyl t-butyl ether, and the like, with azeotropic removal of water.

In a subsequent step, a cyanide source, such as HCN, acetone cyanohydrin, an alkali metal cyanide (NaCN, KCN, etc.), or an alkaline earth metal cyanide (magnesium cyanide, etc.), undergoes conjugate addition to the β-carbon of the α,β-unsaturated malonic acid diester (Formula 19). The reaction is typically carried out in one or more polar protic solvents, including EtOH, MeOH, n-propanol, isopropanol, or polar aprotic solvents, such as DMSO, and the like. Subsequent acid workup yields the cyano-substituted diester (Formula 4). For an application of the method depicted in FIG. 2 to prepare a pregabalin precursor (Formula 12), see U.S. Pat. No. 5,637,767 to Grote et al., which is herein incorporated by reference in its entirety and for all purposes.

The desired (S)- or (R)-enantiomers of any of the compounds disclosed herein may be further enriched through classical resolution, chiral chromatography, or recrystallization. For example, the optically active γ-amino acids (Formula 1 or Formula 9) may be reacted with an enantiomerically-pure compound (e.g., acid or base) to yield a pair of diastereoisomers, each composed of a single enantiomer, which are separated via, say, fractional recrystallization or chromatography. The desired enantiomer is subsequently regenerated from the appropriate diastereoisomer. Additionally, the desired enantiomer often may be further enriched by recrystallization in a suitable solvent when it is it available in sufficient quantity (e.g., typically not much less than about 85% ee, and in some cases, not much less than about 90% ee).

As described throughout the specification, many of the disclosed compounds have stereoisomers. Some of these compounds may exist as single enantiomers (enantiopure compounds) or mixtures of enantiomers (enriched and racemic samples), which depending on the relative excess of one enantiomer over another in a sample, may exhibit optical activity. Such stereoisomers, which are non-superimposable mirror images, possess a stereogenic axis or one or more stereogenic centers (i.e., chirality). Other disclosed compounds may be stereoisomers that are not mirror images. Such stereoisomers, which are known as diastereoisomers, may be chiral or achiral (contain no stereogenic centers). They include molecules containing an alkenyl or cyclic group, so that cis/trans (or Z/E) stereoisomers are possible, or molecules containing two or more stereogenic centers, in which inversion of a single stereogenic center generates a corresponding diastereoisomer. Unless stated or otherwise clear (e.g., through use of stereobonds, stereocenter descriptors, etc.) the scope of the present invention generally includes the reference compound and its stereoisomers, whether they are each pure (e.g., enantiopure) or mixtures (e.g., enantiomerically enriched or racemic).

Some of the compounds may also contain a keto or oxime group, so that tautomerism may occur. In such cases, the present invention generally includes tautomeric forms, whether they are each pure or mixtures.

Many of the compounds described in this disclosure, including those represented by Formula 1 and Formula 9, are capable of forming pharmaceutically acceptable salts. These salts include, without limitation, acid addition salts (including diacids) and base salts. Pharmaceutically acceptable acid addition salts include nontoxic salts derived from inorganic acids such as hydrochloric, nitric, phosphoric, sulfuric, hydrobromic, hydroiodic, hydrofluoric, phosphorous, and the like, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like.

Pharmaceutically acceptable base salts include nontoxic salts derived from bases, including metal cations, such as an alkali or alkaline earth metal cation, as well as amines. Examples of suitable metal cations include, without limitation, sodium cations ($Na^+$), potassium cations ($K^+$), magnesium cations ($Mg^{2+}$), calcium cations ($Ca^{2+}$), and the like. Examples of suitable amines include, without limitation, N,N'-dibenzylethylenediamine, chloroprocaine, choline, diethanolamine, dicyclohexylamine, ethylenediamine, N-methylglucamine, procaine, and t-butyl amine. For a discussion of useful acid addition and base salts, see S. M. Berge et al., "Pharmaceutical Salts," 66 *J. of Pharm. Sci.*, 1-19 (1977); see also Stahl and Wermuth, *Handbook of Pharmaceutical Salts: Properties, Selection, and Use* (2002).

One may prepare a pharmaceutically acceptable acid addition salt (or base salt) by contacting a compound's free base (or free acid) or zwitterion with a sufficient amount of a desired acid (or base) to produce a nontoxic salt. If the salt precipitates from solution, it may be isolated by filtration; otherwise, the salt may be recovered by evaporating the solvent. One may also regenerate the free base (or free acid) by contacting the acid addition salt with a base (or the base salt with an acid). Though certain physical properties of the free base (or free acid) and its respective acid addition salt (or base salt) may differ (e.g., solubility, crystal structure, hygroscopicity, etc.), a compound's free base and acid addition salt (or its free acid and base salt) are otherwise the same for purposes of this disclosure.

Disclosed and claimed compounds may exist in both unsolvated and solvated forms and as other types of complexes besides salts. Useful complexes include clathrates or compound-host inclusion complexes where the compound and host are present in stoichiometric or non-stoichiometric amounts. Useful complexes may also contain two or more organic, inorganic, or organic and inorganic components in stoichiometric or non-stoichiometric amounts. The resulting complexes may be ionized, partially ionized, or non-ionized. For a review of such complexes, see J. K. Haleblian, *J. Pharm. Sci.* 64(8):1269-88 (1975). Pharmaceutically acceptable solvates also include hydrates and solvates in which the crystallization solvent may be isotopically substituted, e.g. $D_2O$, $d_6$-acetone, $d_6$-DMSO, etc. Generally, for the purposes of this disclosure, references to an unsolvated form of a compound also include the corresponding solvated or hydrated form of the compound.

The disclosed compounds also include all pharmaceutically acceptable isotopic variations, in which at least one atom is replaced by an atom having the same atomic number, but an atomic mass different from the atomic mass usually found in nature. Examples of isotopes suitable for inclusion in the disclosed compounds include, without limitation, isotopes of hydrogen, such as $^2H$ and $^3H$; isotopes of carbon, such as $^{13}C$ and $^{14}C$; isotopes of nitrogen, such as $^{15}N$; isotopes of oxygen, such as $^{17}O$ and $^{18}O$; isotopes of phosphorus, such as $^{31}P$ and $^{32}P$; isotopes of sulfur, such as $^{35}S$; isotopes of fluorine, such as $^{18}F$; and isotopes of chlorine, such as $^{36}Cl$. Use of isotopic variations (e.g., deuterium, $^2H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3H$, or $^{14}C$), which may be useful in drug and/or substrate tissue distribution studies.

EXAMPLES

The following examples are intended to be illustrative and non-limiting, and represent specific embodiments of the present invention.

General Materials and Methods

Enzyme screening was carried out using a 96-well plate, which is described in D. Yazbeck et al., *Synth. Catal.* 345: 524-32 (2003), the complete disclosure of which is herein incorporated by reference for all purposes. All enzymes used in the screening plate (see Table 2) were obtained from commercial enzyme suppliers including Amano (Nagoya, Japan), Roche (Basel, Switzerland), Novo Nordisk (Bagsvaerd, Denmark), Altus Biologics Inc. (Cambridge, Mass.), Biocatalytics (Pasadena, Calif.), Toyobo (Osaka, Japan), Sigma-Aldrich (St. Louis, Mo.) and Fluka (Buchs, Switzerland). The screening reactions were performed in an Eppendorf Thermomixer-R (VWR). Subsequent larger scale enzymatic resolutions employed LIPOLASE® 100L and LIPOLASE® 100T, which are available form Novo-Nordisk A/S (CAS no. 9001-62-1).

Nuclear Magnetic Resonance

Three hundred MHz $^1H$ NMR and 75 MHz $^{13}C$ NMR spectra were obtained on a BRUKER 300 UltraShield™ equipped with a 5 mm auto switchable PHQNP probe. Spectra were generally acquired near RT, and standard autolock, autoshim and autogain routines were employed. Samples were usually spun at 20 Hz for 1D experiments. $^1H$ NMR spectra were acquired using 30-degree tip angle pulses, 1.0 s recycle delay, and 16 scans at a resolution of 0.25 Hz/point. The acquisition window was typically 8000 Hz from +18 to −2 ppm (Reference TMS at 0 ppm) and processing was with 0.3 Hz line broadening. Typical acquisition time was 5-10 s. Regular $^{13}C$ NMR spectra were acquired using 30-degree tip angle pulses, 2.0 s recycle delay, and 2048 scans at a resolution of 1 Hz/point. Spectral width was typically 25 KHz from +235 to −15 ppm (Reference TMS at 0 ppm). Proton decoupling was applied continuously and 1 Hz line broadening was applied during processing. Typical acquisition time was 102 min.

Mass Spectrometry

Mass Spectrometry was performed on a HEWLETT PACKARD 1100MSD using HP Chemstation Plus Software. The LC was equipped with an Agilent 1100 quaternary LC system and an Agilent liquid handler as an autosampler. Data were acquired under electron spray ionization with ACN/water (containing 0.1% formic acid) as the solvent (10% ACN to 90%, 7 min). Temperatures: probe was 350° C., source was 150° C. Corona discharge was 3000 V for positive ion and 3000 V for negative ion.

High Performance Liquid Chromatography

High Performance Liquid Chromatography (HPLC) was performed on a series 1100 AGILENT TECHNOLOGIES instrument equipped with an Agilent 220 HPLC auto sampler, quaternary pump, and a UV detector. The LC was PC controlled using HP Chemstation Plus Software. Normal Phase chiral HPLC was performed using Chiral HPLC columns obtained from Chiral Technologies (Exton, Pa.) and Phenomenex (Torrance, Calif.).

Gas Chromatography

Gas Chromatography (GC) was performed on a 110 volt Agilent 6890N network GC system equipped with an FID detector with electrometer, a 7683 Series split/splitless capillary injector, a relay board that monitors four external events, and an inboard printer/plotter. Enantiomeric excess of the diester (Formula 13, $R^3=R^4=Et$) and monoester (Formula 11, $R^3=Et$) were performed using a CHIRALDEX G-TA column (30 m×0.25 mm), with helium carrier gas, and at 135° C. Under such conditions, the monoester decomposed to give (S)-3-cyano-5-methyl-hexanoic acid ethyl ester, and ee was determined based on the decomposition product. The chiral GC columns used in analysis were obtained from Astec, Inc (Whippany, N.J.).

Example 1

Enzyme screening via enzymatic hydrolysis of (R/S)-3-cyano-2-ethoxycarbonyl-5-methyl-hexanoic acid ethyl ester (Formula 20) to yield (3S)-3-cyano-2-ethoxycarbonyl-5-methyl-hexanoic acid (Formula 21)

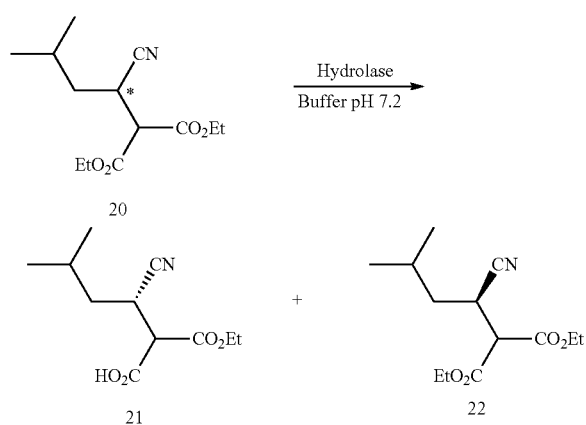

Enzyme screening was carried out using a screening kit comprised of individual enzymes deposited in separate wells of a 96-well plate, which was prepared in advance in accordance with a method described in D. Yazbeck et al., *Synth. Catal.* 345:524-32 (2003). Each of the wells had an empty volume of 0.3 ml (shallow well plate). One well of the 96-well plate contained only phosphate buffer (10 µL, 0.1 M, pH 7.2), another well contained only ACN (10 µL), and each of the remaining wells contained one of the 94 enzymes listed in Table 2 (10 µL, 100 mg/mL). Prior to use, the screening kit was removed from storage at −80° C. and the enzymes were allowed to thaw at RT for about 5 min. Potassium phosphate buffer (85 µL, 0.1 M, pH 7.2) was dispensed into each of the wells using a multi-channel pipette. Concentrated substrate (Formula 20, 5 µL) was subsequently added to each well via a multi-channel pipette and the 96 reaction mixtures were incubated at 30° C. and 750 rpm. The reactions were quenched and sampled after 24 h by transferring each of the reaction mixtures into separate wells of a second 96-well plate. Each of the wells had an empty volume of 2 mL (deep well plate) and contained EtOAc (1 mL) and HCl (1N, 100 µL). The components of each well were mixed by aspirating the well contents with a pipette. The second plate was centrifuged and 100 µL of the organic supernatant was transferred from each well into separate wells of a third 96-well plate (shallow plate). The wells of the third plate were subsequently sealed using a penetrable mat cover. Once the wells were sealed, the third plate was transferred to a GC system for determination of optical purity (ee).

Table 3 lists enzyme, trade name, supplier, and E value for some of the enzymes that were screened. For a given enzyme, the E value may be interpreted as the relative reactivity of a pair of enantiomers (substrates). The E values listed in Table 3 were calculated from HPLC data (fractional conversion, $\chi$, and ee) using a computer program called Ee2, which is available from the University of Graz. Generally, enzymes exhibiting S-selectivity and an E value of about 35 or greater are suitable for scale-up.

TABLE 3

Results from Screening Reactions of Example 1

| Enzyme | Trade name | Supplier | E Value |
|---|---|---|---|
| S-Selective | | | |
| *Thermomyces lanuginosus* Lipase | Lipolase | Novozymes | >200 |
| *Rhizopus delemar* Lipase | Lipase D | Amano | >200 |
| *Rhizopus niveus* Lipase | L-9406 | Sigma | 66 |
| *Rhizomucor miehei* Esterase | 46059 | Fluka | 52 |
| *Pseudomonas* sp. Lipase | 103 | Biocatalytics | 51 |
| *Rhizomucor miehei* Lipase | Palatase 20000 | Novozymes | 41 |
| *Rhizopus oryzae* Lipase | FAP15 | Amano | 35 |
| *Candida antarctica* Lipase -A | CAL-A | Novozymes | 5 |
| *Candida antarctica* Lipase -B | CAL-B, Chirazyme L-2 | Novozymes | 3 |
| Marginally S-Selective | | | |
| Pig liver Esterase | PLE-AS | Biocatalytics | <2 |
| Enteropeptidase | | Sigma | <2 |
| Porcine kidney Acylase | | Sigma | <2 |
| Cholesterol Esterase | | Biocatalytics | <2 |
| R-Selective | | | |
| *Streptomyces griseus* Protease | | Sigma | 20 |
| *Streptomyces* sp. Protease | 118 | Biocatalytics | 11 |

Example 2

Enzymatic resolution of (R/S)-3-cyano-2-ethoxycarbonyl-5-methyl-hexanoic acid ethyl ester (Formula 20) to yield (3S)-3-cyano-2-ethoxycarbonyl-5-methyl-hexanoic acid potassium salt (Formula 23) and (R)-3-cyano-2-ethoxycarbonyl-5-methyl-hexanoic acid ethyl ester (Formula 22)

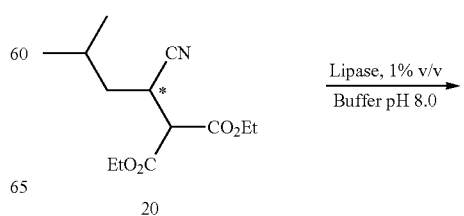

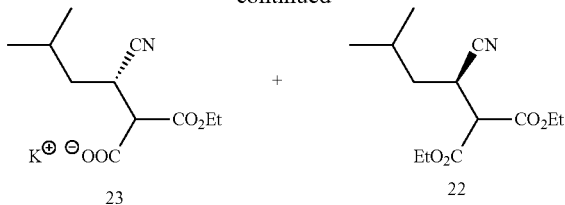

A reactor (392 L) equipped with overhead stirring was charged with potassium phosphate buffer (292.2 L, 10 mM, pH 8.0) and LIPOLASE® 100L, type EX (3.9 L). The mixture was stirred at 800 RPM for 1 min and KOH (2 M) was added to adjust the pH to 8.0. (R/S)-3-Cyano-2-ethoxycarbonyl-5-methyl-hexanoic acid ethyl ester (Formula 20, 100 kg) was added, and the resulting mixture was titrated with NaOH aq (50%) during hydrolysis to maintain a pH of 8.0. The extent of reaction was monitored by HPLC ($C_{18}$ column, 4.6 mm×150 mm, detection at 200 nm). Upon reaching a conversion of about 40-45% (e.g., after about 24 h) the reaction mixture was transferred to a separatory funnel. The aqueous mixture was extracted with heptane (205 L). EtOH (absolute) was added (up to about 5% v/v) to disrupt a light emulsion that formed, and the aqueous and organic layers were separated. The extraction step was repeated twice, and the aqueous layer containing (3S)-3-cyano-2-ethoxycarbonyl-5-methyl-hexanoic acid potassium salt (Formula 23) may be further concentrated under vacuum (e.g., 25-50% of its original volume). The organic layers containing (R)-3-cyano-2-ethoxycarbonyl-5-methyl-hexanoic acid ethyl ester (Formula 22) were combined, dried, and concentrated. The resulting diethyl ester was subsequently racemized in accordance with Example 6. MS m/z [M+H]$^+$227. $^1$H NMR (300 MHz, D$_2$O): δ 2.35 (dd, 6H), 2.70 (t, 3H), 2.85 (m, 1H), 2.99 (m, 1H), 3.25 (m, 1H), 4.75 (m, 1H), 5.60 (q, 2H). $^{13}$C NMR (75 ppm, D$_2$O) δ 172.19, 171.48, 122.85, 62.70, 59.49, 40.59, 31.83, 27.91, 23.94, 21.74, 14.77.

Example 3

Enzymatic resolution of (R/S)-3-cyano-2-ethoxycarbonyl-5-methyl-hexanoic acid ethyl ester (Formula 20) to yield (3S)-3-cyano-2-ethoxycarbonyl-5-methyl-hexanoic acid potassium salt (Formula 23) and (R)-3-cyano-2-ethoxycarbonyl-5-methyl-hexanoic acid ethyl ester (Formula 22)

A reactor (3.92 L) equipped with overhead stirring is charged with calcium acetate buffer (1.47 L, 100 mM, pH 7.0) and (R/S)-3-cyano-2-ethoxycarbonyl-5-methyl-hexanoic acid ethyl ester (Formula 20, 1 kg). The mixture is stirred at 1100 RPM for 5 min and KOH (5 M) is added to adjust the pH to 7.0. LIPOLASE® 100L, type EX (75 mL) is added and the resulting mixture is titrated with KOH (5 M) during hydrolysis to maintain a pH of 7.0. The extent of reaction is monitored by HPLC ($C_{18}$ column, 4.6 mm×150 mm, detection at 200 nm). Upon reaching a conversion of about 42% to 45% (e.g., after about 20-25 h) the reaction mixture is transferred to a separatory funnel. The aqueous mixture is extracted with hexane (100% v/v). EtOH (absolute) is added (up to about 5% v/v) to disrupt a light emulsion that forms, and the aqueous and organic layers are separated. The extraction step is repeated twice to obtain an aqueous layer containing (3S)-3-cyano-2-ethoxycarbonyl-5-methyl-hexanoic acid potassium salt (Formula 23), which may be used in subsequent transformations without isolation. The organic layers containing (R)-3-cyano-2-ethoxycarbonyl-5-methyl-hexanoic acid ethyl ester (Formula 22) are combined, dried, and concentrated. The resulting diethyl ester is subsequently racemized in accordance with Example 6.

Example 4

Preparation of (S)-4-isobutyl-2-oxo-pyrrolidine-3-carboxylic acid (Formula 10) from (3S)-3-cyano-2-ethoxycarbonyl-5-methyl-hexanoic acid potassium salt (Formula 23)

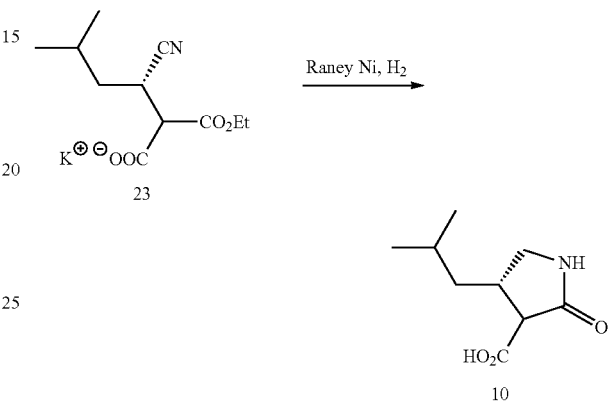

A vessel was charged with an aqueous solution containing (3S)-3-cyano-2-ethoxycarbonyl-5-methyl-hexanoic acid potassium salt (Formula 23, 411 L from Example 2). Raney Nickel (50% aq solution, Sigma-Aldrich) was added to the mixture, and hydrogen gas was introduced into the vessel over a 20 h period to maintain a pressure of 50 psig in the vessel headspace throughout reaction. The hydrogenation reaction was monitored by H$_2$ uptake and HPLC analysis ($C_{18}$ column, 4.6 mm×150 mm, detection at 200 nm) of the vessel contents. Following reaction, the aqueous mixture was filtered to remove the Raney Ni catalyst. The pH of the concentrated solution was adjusted to 3.0 using 37% HCl (about 14 L). The resulting solution was extracted three times with EtOAc (50% v/v). The combined organic layers were concentrated under vacuum to afford (S)-4-isobutyl-2-oxo-pyrrolidine-3-carboxylic acid (Formula 10). MS ink [M+H]$^+$ 186.1130. $^{13}$C NMR (75 ppm, CDCl$_3$) δ 175.67, 172.23, 54.09, 47.62, 43.69, 37.22, 26.31, 23.34, 22.54. Yield 40-42%; 97% ee.

Example 5

Preparation of pregabalin (Formula 9) from (S)-4-isobutyl-2-oxo-pyrrolidine-3-carboxylic acid (Formula 10)

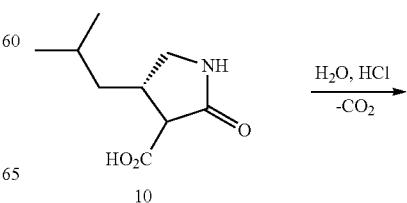

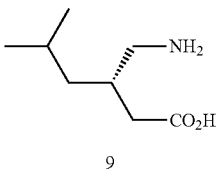
9

A reactor vessel (60 L) was charged with (S)-4-isobutyl-2-oxo-pyrrolidine-3-carboxylic acid (Formula 10), HCl (36-38%, 30 L), and water (29 L). HOAc (1 L) was added to the solution and the resulting slurry was heated for 36-38 h at 80° C. and for an additional 6 h at 110° C. The extent of reaction was monitored by HPLC ($C_{18}$ column, 4.6 mm×150 mm, detection at 200 nm). Water and excess HCl were evaporated to afford an oil, which was washed with MTBE (2×15 L). Water was added to the oil and the mixture was stirred until the solution cleared. The pH of the solution was adjusted to 5.2-5.5 using KOH (about 6 kg), which resulted in the precipitation of pregabalin. The mixture was heated to 80° C. and subsequently cooled to 4° C. After 10 h, crystalline pregabalin was filtered and washed with IPA (12 L). The filtrate was concentrated under vacuum to afford a residual oil. Water (7.5 L) and EtOH (5.0 L) were added to the residual oil and the resulting mixture was heated to 80° C. and then cooled to 4° C. After 10 h, a second crop of pregabalin crystals were filtered and washed with IPA (1 L). The combined pregabalin crystals were dried in a vacuum oven at 45° C. for 24 h. MS m/z [M+H]$^+$ 160.1340. $^1$H NMR (300 MHz, $D_2O$): δ 2.97 (dd, J=5.4, 12.9 Hz, 1H), 2.89 (dd, J=6.6, 12.9 Hz, 1H), 2.05-2.34 (m, 2H), 1.50-1.70 (sept, J=6.9 Hz, 1H), 1.17 (t, J=7.0 Hz, 2H), 0.85 (dd, J=2.2, 6.6 Hz, 6H). $^{13}$C NMR (75 ppm, $D_2O$) δ 181.54, 44.32, 41.28, 32.20, 24.94, 22.55, 22.09. Yield 80-85%; ee>99.5%.

Example 6

Preparation of (R/S)-3-cyano-2-ethoxycarbonyl-5-methyl-hexanoic acid ethyl ester (Formula 20) via racemization of (R)-3-cyano-2-ethoxycarbonyl-5-methyl-hexanoic acid ethyl ester (Formula 22)

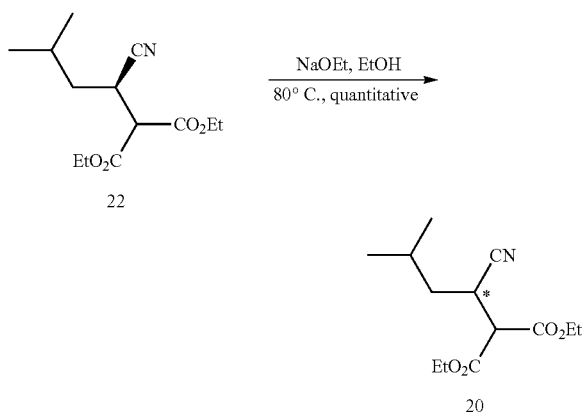

A reactor was charged with (R)-3-cyano-2-ethoxycarbonyl-5-methyl-hexanoic acid ethyl ester (Formula 22, 49.5 kg) and EtOH (250 L). Sodium ethoxide (21% w/w in EtOH, 79.0 L, 1.1 eq) was added to the mixture, which was heated to 80° C. for 20 h. After completion of the reaction, the mixture was allowed to cool to RT and was neutralized by adding HOAc (12.2 L). Following evaporation of the EtOH, MTBE (150 L) was added to the mixture, and the resulting solution was filtered and evaporated to afford (R/S)-3-cyano-2-ethoxycarbonyl-5-methyl-hexanoic acid ethyl ester (Formula 20) in quantitative yield.

Example 7

Preparation (S)-3-cyano-5-methyl-hexanoic acid ethyl ester (Formula 24) from (3S)-3-cyano-2-ethoxycarbonyl-5-methyl-hexanoic acid (Formula 21)

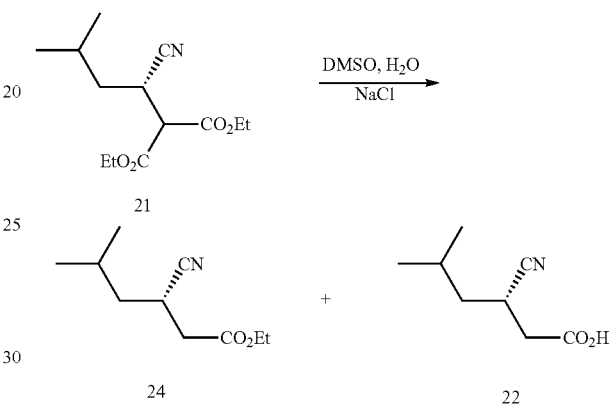

A 50 mL round bottomed flask was charged with (3S)-3-cyano-2-ethoxycarbonyl-5-methyl-hexanoic acid (Formula 21, 3.138 g, 13.79 mmol), NaCl (927 mg, 1.15 eq), de-ionized water (477 μL, 1.92 eq) and DMSO (9.5 mL). The resulting mixture was heated to 88° C. and maintained at that temperature for 17 h. A sample was taken for LC and LC/MS analyses, which showed the presence of the starting material (Formula 21) and the products (Formula 24 and Formula 25). The temperature of the mixture was subsequently increased to 135° C. and allowed to react for an additional 3.5 h. A second sample was taken for LC and LC/MS analysis, which showed the absence of starting material (Formula 21) and showed, in addition to the desired products (Formula 24 and Formula 25), the presence of unidentified byproducts. (S)-3-cyano-5-methyl-hexanoic acid ethyl ester (Formula 24): 97.4% ee after 88° C.; 97.5% ee after 135° C.

Example 8

Determination of the optical purity (ee) of (S)-4-isobutyl-2-oxo-pyrrolidine-3-carboxylic acid (Formula 10)

The optical purity of (S)-4-isobutyl-2-oxo-pyrrolidine-3-carboxylic acid (Formula 10) was determined via a derivatization method. A sample of (S)-4-isobutyl-2-oxo-pyrrolidine-3-carboxylic acid was esterified with EtOH in the presence of a catalytic amount of dry HCl in dioxane at 70° C. The resulting lactam ester was analyzed by HPLC (CHIRALPAK AD-H, 4.6 mm×250 mm) using a mobile phase of hexane and EtOH (95:5), a flow rate of 1.0 mL/min, injection volume of 10 μL, column temperature of 35° C., and detection at 200 nm.

Example 9

Determination of the Optical Purity (ee) of Pregabalin (Formula 9)

The optical purity of pregabalin was analyzed via a derivatization method. A sample of pregabalin was derivatized with Marfey's reagent (1-fluoro-2-4-dinitrophenyl-5-L-alanine amide) and then analyzed by HPLC (LUNA $C_{18}$(2) column, 0.46 mm×150 mm, 3 μm) using a mobile phase of aqueous $NaPO_4$ (20 nM, pH 2.0) and ACN (90:10 for 10 min, 10:90 for 3 min, 90:10 for 5 min), a flow rate of 1.2 mL/min, an injection volume of 10 μL, column temperature of 35° C., and detection at 200 nm.

Example 10

Enzymatic resolution of (R/S)-3-cyano-2-ethoxycarbonyl-5-methyl-hexanoic acid ethyl ester (Formula 20) to yield (3S)-3-cyano-2-ethoxycarbonyl-5-methyl-hexanoic acid sodium salt (Formula 23) and (R)-3-cyano-2-ethoxycarbonyl-5-methyl-hexanoic acid ethyl ester (Formula 22)

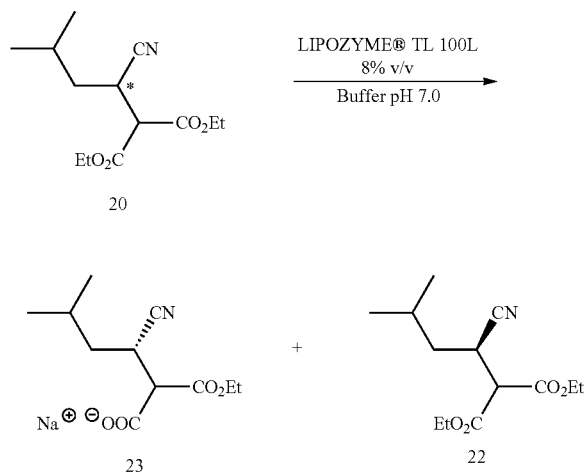

A reactor (16000 L) equipped with overhead stirring is charged with calcium acetate (254 kg), deionized water (1892.7 kg) and LIPOZYME® TL 100 L (food grade LIPOLASE®, 983.7 kg). After complete mixing, (R/S)-3-cyano-2-ethoxycarbonyl-5-methyl-hexanoic acid ethyl ester (Formula 20, 9000 kg, 85% purity assay) is charged and the mixture is stirred for 24 h. NaOH (2068 kg of a 30% solution) is added over the course of the reaction to maintain the pH at 7.0. The extent of reaction is monitored by HPLC ($C_{18}$ column, 4.6 mm×150 mm, detection at 200 nm). Upon reaching a conversion of about 42% to 45% (e.g., after about 20-25 h) the titrator and stirring are stopped. The organic phase is immediately separated and the aqueous phase is washed twice with toluene (780 kg). The aqueous layer containing (3S)-3-cyano-2-ethoxycarbonyl-5-methyl-hexanoic acid sodium salt (Formula 23) is used in subsequent transformations (Example 11) without isolation. The organic layers containing (R)-3-cyano-2-ethoxycarbonyl-5-methyl-hexanoic acid ethyl ester (Formula 22) are combined and concentrated. The resulting diethyl ester is subsequently racemized in accordance with Example 6.

Example 11

Preparation (S)-3-cyano-5-methyl-hexanoic acid ethyl ester (Formula 24) from (3S)-3-cyano-2-ethoxycarbonyl-5-methyl-hexanoic acid sodium salt (Formula 23)

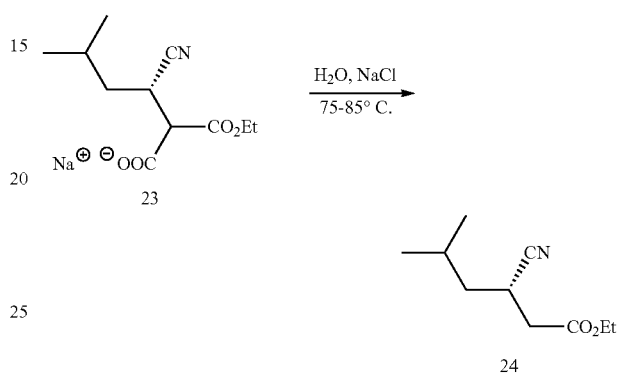

A reactor (16000 L) equipped with overhead stirring is charged with the final aqueous solution from Example 10 (9698.6 L, containing (3S)-3-cyano-2-ethoxycarbonyl-5-methyl-hexanoic acid sodium salt, Formula 23), NaCl (630 kg) and toluene (900 L). The mixture is stirred for 2 h under refluxing conditions (75-85° C.). The stirring is stopped; the organic phase is immediately separated and the aqueous phase is washed twice with toluene (900 L). The organic layers, which contain (S)-3-cyano-5-methyl-hexanoic acid ethyl ester (Formula 24) are combined and concentrated. The ethyl ester (Formula 24) is subsequently hydrolyzed in accordance with Example 12.

Example 12

Preparation of (S)-3-cyano-5-methyl-hexanoic acid potassium salt (Formula 26) from (S)-3-cyano-5-methyl-hexanoic acid ethyl ester (Formula 24)

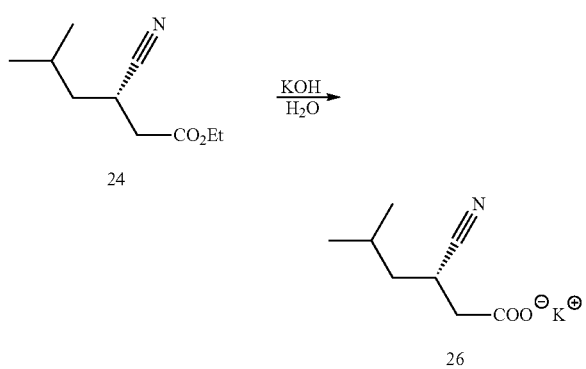

A reactor (12000 L) equipped with overhead stirring is charged with (S)-3-cyano-5-methyl-hexanoic acid ethyl ester (Formula 24, 2196 L from Example 11). KOH (1795.2 kg, 45% solution, w/w) and H₂O (693.9 kg) are added to the reaction mixture with vigorous stirring. The temperature is maintained at 25° C. After 4 h, the reaction mixture is charged to a hydrogenation vessel (Example 13) with no further work-up.

Example 13

Preparation of pregabalin (Formula 9) from (S)-3-cyano-5-methyl-hexanoic acid potassium salt (Formula 26)

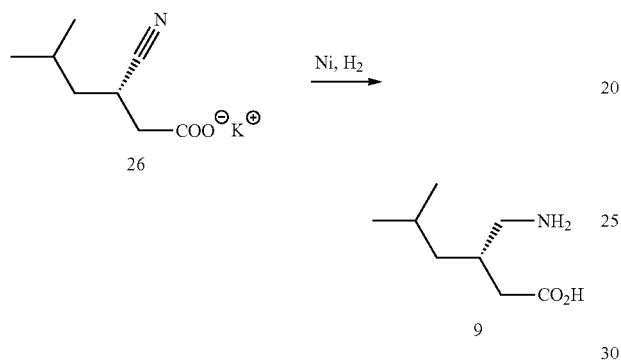

A hydrogenator (12000 L) is charged with water (942.1 L) and with the reaction mixture from Example 12, which contains (S)-3-cyano-5-methyl-hexanoic acid potassium salt (Formula 26, 4122.9 L). A Raney nickel suspension (219.6 kg, 50% w/w in H₂O) is added. The hydrogenation is conducted under 50 psig at 35° C. After 6 h, the Raney nickel is filtered and the resulting filtrate is transferred to a reactor (16000 L) for crystallization. After adding H₂O (1098 L), the pH of the solution is adjusted to 7.0-7.5 using HOAc (864.7 kg). The resulting precipitate is filtered and washed once with H₂O (549 L) and twice with IPA (2,586 L each). The solid is recrystallized with IPA (12296 L) and H₂O (6148 L). The mixture is heated to 70° C. and subsequently cooled to 4° C. After 5-10 h, the crystalline solid is filtered, washed with IPA (5724 L), and dried in a vacuum oven at 45° C. for 24 h to give pregabalin as a white crystalline solid (1431 kg, 30.0% overall yield, 99.5% purity and 99.75% ee).

It should be noted that, as used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. It is to be understood that the above description is intended to be illustrative and not restrictive. Many embodiments will be apparent to those of skill in the art upon reading the above description. Therefore, the scope of the invention should be determined with references to the appended claims and includes the full scope of equivalents to which such claims are entitled. The disclosures of all articles and references, including patents, patent applications and publications, are herein incorporated by reference in their entirety and for all purposes.

What is claimed is:
1. A method of making a compound of Formula 9,

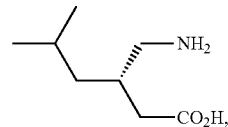

or a pharmaceutically acceptable complex, salt, solvate or hydrate thereof, the method comprising:
(a) reducing a cyano moiety of a compound of Formula 14,

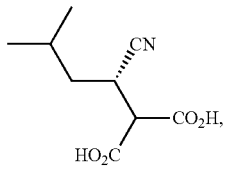

or a salt thereof, to yield a compound of Formula 15,

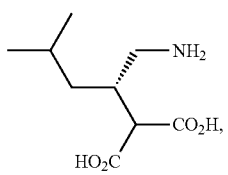

or a salt thereof;
(b) decarboxylating the compound of Formula 15 or a salt thereof to yield the compound of Formula 9, or a salt thereof;
(c) optionally converting the compound of Formula 9 or a salt thereof into a pharmaceutically acceptable complex, salt, solvate or hydrate;
(d) wherein the compound of Formula 14 is prepared by hydrolyzing a compound of Formula 11

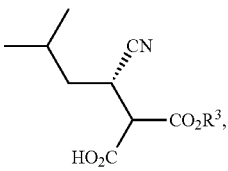

or a salt thereof, in which R³ is represented by C$_{1-12}$ alkyl, C$_{3-12}$ cycloalkyl, or aryl-C$_{1-6}$ alkyl, and;
(e) the compound of formula 11 is prepared by a method further comprising: contacting a compound of Formula 12,

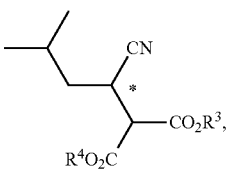

with an enzyme to yield the compound of Formula 11 and a compound of Formula 13

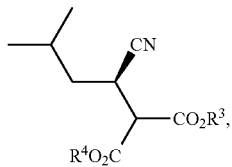

wherein the enzyme is adapted to enantioselectively hydrolyze the compound of Formula 12 to the compound of Formula 11 or a salt thereof;

$R^3$ in Formula 12 and Formula 13 is as defined in Formula 11; and $R^4$ in Formula 12 and Formula 13 is the same as or different than $R^3$ and is $C_{1-12}$ alkyl, $C_{3-12}$ cycloalkyl, or aryl-$C_{1-6}$ alkyl.

* * * * *